US005750550A

United States Patent [19]

Eissenstat et al.

[11] Patent Number: 5,750,550
[45] Date of Patent: May 12, 1998

[54] 2-(PYRAZOL-5-YL-OXYMETHYL)-1,2-BENZISOTHIAZOL-3 (2H)-ONE 1, 1-DIOXIDES AND COMPOSITIONS AND METHOD OF USE THEREOF

[75] Inventors: Michael A. Eissenstat, Frederick, Md.; Gee-Hong Kuo, Scotch Plains Township, Union County; Ranjit C. Desai, Kendall Park, both of N.J.; Dennis J. Hlasta, Lower Salford Township, Montgomery County, Pa.; John J. Court, Littleton, Mass.

[73] Assignee: Sanofi, Paris, France

[21] Appl. No.: 529,121

[22] Filed: Sep. 15, 1995

[51] Int. Cl.$^6$ .................. A61K 31/425; C07D 275/04
[52] U.S. Cl. ............................ 514/373; 548/210
[58] Field of Search .................. 548/210; 514/373

[56] References Cited

U.S. PATENT DOCUMENTS 5,578,623  11/1996  Dunlap et al. ............... 514/373
5,596,012  1/1997   Dunlap et al. ............... 514/373

Primary Examiner—Johann Richter
Assistant Examiner—Laura Cross Lutz
Attorney, Agent, or Firm—Michael D. Alexander; Mary P. Bauman; Paul E. Dupont

[57] ABSTRACT 2-(Pyrazol-5-yl-oxymethyl)-1,2-benzisothiazol-3(2H)-one 1,1-dioxides, pharmaceutical compositions containing them and methods for the treatment of degenerative diseases utilizing them.

29 Claims, No Drawings

5,750,550

2-(PYRAZOL-5-YL-OXYMETHYL)-1,2-BENZISOTHIAZOL-3 (2H)-ONE 1, 1-DIOXIDES AND COMPOSITIONS AND METHOD OF USE THEREOF

BACKGROUND OF THE INVENTION (a) Field of The Invention

The invention relates to 2-(pyrazol-5-yl-oxymethyl)-1,2-benzisothiazol-3(2H)-one 1,1-Dioxides, to pharmaceutical compositions containing the same and to the method of use thereof in the treatment of degenerative diseases.

(b) Information Disclosure Statement

The inhibition of proteolytic enzymes by nontoxic reagents is useful in the treatment of degenerative disorders, such as emphysema, rheumatoid arthritis and pancreatitis, in which proteolysis is a substantive element.

Protease inhibitors are widely utilized in biomedical research. Serine proteases are the most widely distributed class of proteolytic enzymes. Some serine proteases are characterized as chymotrypsin-like or elastase-like based upon their substrate specificity.

Chymotrypsin and chymotrypsin-like enzymes normally cleave peptide bonds in proteins at a site at which the amino acid residue on the carboxyl side is typically Trp, Tyr, Phe, Met, Leu or another amino acid residue which contains aromatic or large alkyl side chains.

Elastase and elastase-like enzymes normally cleave peptide bonds at a site at which the amino acid residue on the carboxyl side of the bond is typically Ala, Val, Ser, Leu or other similar, smaller amino acids.

Both chymotrypsin-like and elastase-like enzymes are found in leukocytes, mast cells and pancreatic juice in higher organisms, and are secreted by many types of bacteria, yeast and parasites.

Cha, Biochem. Pharmacol., 1975, 24, 2177–2185, discusses kinetic approaches to the study of the binding of inhibitors to macromolecules, such as enzymes, and methods for the determination of such parameters as the inhibition constants, reaction rates and bound and unbound enzyme concentrations.

Dunlap et al., U.S. Pat. No. 5,236,917, issued Aug. 17, 1993, Dunlap et al., U.S. Pat. No. 5,371,074, issued Dec. 6, 1994, Dunlap et al., PCT Application WO 90/13549, published Nov. 15, 1990, Dunlap et al., European Patent Application 471,756, published Feb. 26, 1992 and Dunlap et al., European Patent Application 542,372, published May 19, 1993, disclose 2-substituted saccharin derivatives having the formula:

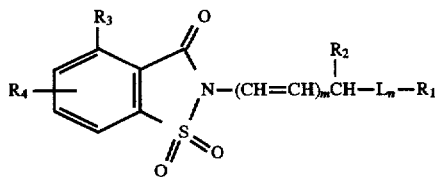

wherein:

L is —O—, —S—, —SO— or —SO$_2$—;

m and n are each independently 0 or 1; and

R$_1$, R$_2$, R$_3$ and R$_4$ are a wide variety of substituents. Specifically disclosed is 2-(1-phenyl-4-methoxycarbonylimidazol-2-yl-thiomethyl) saccharin (example 30AR). The compounds are said to possess protease enzyme inhibitory activity and to be useful in the treatment of degenerative diseases.

Dunlap et al., European Patent Application 542,371, published May 19, 1993, and Dunlap et al., U.S. Pat. No. 5,380,737, issued Jan. 10, 1995, disclose compounds of the formula:

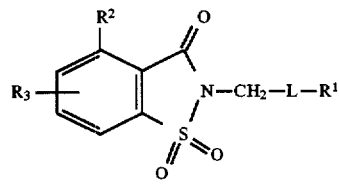

wherein:

L is N, O, or SO$_n$ wherein n is 0, 1 or 2;

L-R$^1$ is a leaving group which is defined in terms of the pKa of the conjugate acid thereof; and R$^2$ and R$^3$ are a wide variety of substituents. The compounds are said to inhibit the enzymatic activity of proteolytic enzymes and to be useful in the treatment of degenerative diseases.

SUMMARY OF THE INVENTION

The invention relates to compounds of the Formula I:

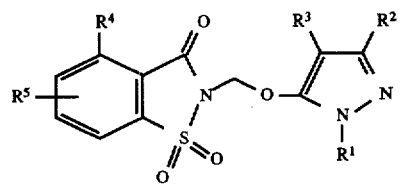

wherein:

R$^1$ is lower-alkyl, phenyl (or phenyl substituted by from one to three, the same or different, substituents selected from the group consisting of nitro, halogen, lower-alkoxy, hydroxy, trifluoromethyl and lower-alkyl), a 5- or 6-membered monocyclic aromatic heterocycle which contains from one to two nitrogen atoms (or said 5- or 6-membered monocyclic aromatic heterocycle substituted on any available carbon atom thereof by nitro, halogen, lower-alkoxy, trifluoromethyl, hydroxy or lower-alkyl), a 9- or 10-membered bicyclic aromatic heterocycle which contains from one to two nitrogen atoms (or said 9- or 10-membered bicyclic aromatic heterocycle substituted on any available carbon atom thereof by nitro, halogen, lower-alkoxy, trifluoromethyl, hydroxy or lower-alkyl), phenyl-lower-alkyl, or cycloalkyl;

R$^2$ is hydrogen, lower-alkyl, lower-alkoxy, phenyl (or phenyl substituted by from one to five, the same or different, substituents selected from the group consisting of halogen, lower-alkyl, lower-alkoxy, nitro, hydroxy and trifluoromethyl), trihalomethyl, lower-alkoxycarbonyl, pyridyl, carboxy, —C(O)N(R)(alkylene)—NB (wherein R is hydrogen or lower-alkyl and NB is 1-pyrrolidinyl or dilower-alkylamino), halogen, or cyano;

R$^3$ is hydrogen, halogen, or lower-alkyl;

R$^4$ is lower-alkyl, lower-alkoxy, or cycloalkyl; and

R$^5$ is hydrogen, or from one to two substituents in any of the 5-, 6-, or 7- positions selected from the group

3 consisting of lower-alkoxy, —O—$(CH_2)_n$-[5-
$((CH_2)_n$—N(lower-alkyl)$_2$)-2-furanyl],
benzyloxycarbonyl-lower-alkoxy, lower-
alkoxycarbonyl-lower-alkoxy, carboxylower-alkoxy,
hydroxy, —O—(lower-alkyl)—C(O)N(R') (alkylene)N
(lower-alkyl)$_2$, —O—$(CH_2)_n$-[5-(C(O)OCH$_2$-phenyl-
R")-2-furanyl], —O—$(CH_2)_n$-(5-carboxy-2-furanyl),
and —O—$(CH_2)_n$-[5- (C(O)N(R'")(alkylene)-N-
(lower-alkyl)$_2$)-2-furanyl]; wherein n is an integer from
one to four; R' is hydrogen or lower-alkyl; R" is
hydrogen, lower-alkyl, or lower-alkoxy; and R'" is
hydrogen or lower-alkyl; or a pharmaceutically accept-
able acid-addition salt of basic members thereof, or a
pharmaceutically acceptable base-addition salt of
acidic members thereof.

The compounds of the present invention inhibit the activ-
ity of serine proteases, specifically human leukocyte
elastase, and are thus useful in the treatment of degenerative
disease conditions such as emphysema, rheumatoid arthritis,
pancreatitis, cystic fibrosis, chronic bronchitis, adult respi-
ratory distress syndrome, inflammatory bowel disease,
psoriasis, bullous pemphigoid, periodontal disease, and
alpha-1-antitrypsin deficiency.

Preferred compounds of the Formula I above are those
wherein:

$R^1$ is lower-alkyl, phenyl (or phenyl substituted by from
one to two, the same or different, substituents selected
from the group consisting of nitro, halogen, and lower-
alkoxy), a 5- or 6-membered monocyclic aromatic
heterocycle selected from the group consisting of
pyridyl, pyridazinyl, pyrazinyl, pyrimidinyl, pyrrolyl,
pyrazolyl, and imidazolyl (or said 5- or 6-membered
monocyclic aromatic heterocycle substituted on any
available carbon atom thereof by halogen,
trifluoromethyl, or lower-alkyl), a 9- or 10-membered
bicyclic aromatic heterocycle selected from the group
consisting of quinolinyl, isoquinolinyl, benzimidazolyl,
quinoxalinyl, quinazolinyl, indolyl, and indazolyl (or
said 9- or 10-membered bicyclic aromatic heterocycle
substituted on any available carbon atom thereof by
halogen, trifluoromethyl, or lower-alkyl), phenyl-
lower-alkyl, or cycloalkyl;

$R^2$ is hydrogen, lower-alkyl, phenyl (or phenyl substituted
by from one to five, the same or different, halogen
substituents), trihalomethyl, lower-alkoxycarbonyl,
pyridyl, carboxy, —C(O)N(R)(alkylene)—NB
(wherein R is hydrogen or lower-alkyl and NB is
1-pyrrolidinyl or dilower-alkylamino), halogen, or
cyano;

$R^3$ is hydrogen or halogen;

$R^4$ is lower-alkyl or lower-alkoxy; and $R^5$ is from one to two substituents in any of the 5-, 6-, or
7- positions selected from the group consisting of
lower-alkoxy, —O—$(CH_2)_n$-[5-$((CH_2)_n$—N(lower-
alkyl)$_2$)-2-furanyl], benzyl oxycarbonyl-lower-alkoxy,
carboxylower-alkoxy, hydroxy, —O—(lower-alkyl)—
C(O)N(R')(alkylene)N(lower-alkyl)$_2$, —O—$(CH_2)_n$-
[5-(C(O)OCH$_2$-phenyl-R")-2-furanyl], —O—$(CH_2)_n$-
(5-carboxy-2-furanyl), and —O—$(CH_2)_n$-[5-(C(O)N
(R'")(alkylene)-N-(lower-alkyl)$_2$)-2-furanyl]; wherein
n is one; R' is lower-alkyl; R" is lower-alkoxy; and R'"
is lower-alkyl.

Particularly preferred compounds of the Formula I above
are those wherein:

$R^1$ is lower-alkyl, phenyl (or phenyl substituted by from
one to two, the same or different, substituents selected

4 from the group consisting of nitro, halogen, and lower-
alkoxy), a 5- or 6-membered monocyclic aromatic
heterocycle selected from the group consisting of
pyridyl, pyridazinyl, and pyrimidinyl (or said 5- or
6-membered monocyclic aromatic heterocycle substi-
tuted on any available carbon atom thereof by halogen,
trifluoromethyl, or lower-alkyl), quinolinyl,
isoquinolinyl, phenyl-lower-alkyl, or cycloalkyl;

$R^2$ is hydrogen, methyl, phenyl, pentafluorophenyl,
trifluoromethyl, ethoxycarbonyl, 4-pyridyl, carboxy,
—C(O)N(R)(CH$_2$)$_2$—NB (wherein R is hydrogen or
methyl and NB is 1-pyrrolidinyl or diethylamino),
chloro, tertbutoxycarbonyl, or cyano;

$R^3$ is hydrogen or chloro;

$R^4$ is isopropyl or ethoxy; and $R^5$ is one substituent in the 6-position selected from the
group consisting of lower-alkoxy, —O—$(CH_2)_n$-[5-(
$(CH_2)_n$—N(lower-alkyl)$_2$)-2-furanyl],
benzyloxycarbonyl-lower-alkoxy, carboxylower-
alkoxy, hydroxy, —O—(lower-alkyl)—C(O)N(R')-
(alkylene)N(lower-alkyl)$_2$, —O—$(CH_2)_n$-[5-(C(O)
OCH$_2$-phenyl-R")-2-furanyl], —O—$(CH_2)_n$-(5-
carboxy-2-furanyl), and —O—$(CH_2)_n$-[5-(C(O)N(R'")
(alkylene)-N-(lower-alkyl)$_2$)-2-furanyl]; wherein n is
one; R' is lower-alkyl; R" is lower-alkoxy; and R'" is
lower-alkyl.

The invention further relates to a pharmaceutical compo-
sition for the treatment of degenerative diseases which
comprises an effective proteolytic enzyme inhibiting amount
of a compound of the Formula I together with a pharma-
ceutically acceptable carrier, adjuvant, diluent or vehicle.

The invention further relates to a method for the treatment
of degenerative diseases which comprises administering to a
patient in need of such treatment an effective proteolytic
enzyme inhibiting amount of a compound of the Formula I.

DETAILED DESCRIPTION INCLUSIVE OF PREFERRED EMBODIMENTS

The term lower-alkyl as used herein means linear or
branched hydrocarbon chains having from one to about five
carbon atoms and thus includes methyl, ethyl, propyl,
isopropyl, n-butyl, sec-butyl, tert-butyl, 3-methylpropyl,
3-methylbutyl, n-pentyl, and the like.

The term lower-alkoxy as used herein means linear or
branched alkyloxy substituents having from one to about
five carbon atoms and thus includes methoxy, ethoxy,
propoxy, isopropoxy, n-butoxy, sec-butoxy, tert-butoxy,
3-methylpropoxy, 3-methylbutoxy, n-pentyloxy, and the
like.

The term halogen, halo, or halide as used herein means
chlorine, bromine, iodine, and fluorine.

The term 5- or 6-membered monocyclic aromatic hetero-
cycle as used herein refers to those heterocycles which
contain from one to two nitrogen atoms such as pyridyl,
pyridazinyl, pyrazinyl, pyrimidinyl, pyrrolyl, pyrazolyl,
imidazolyl, and the like.

The term 9- or 10-membered bicyclic aromatic hetero-
cycle as used herein refers to those heterocycles which
contain from one to two nitrogen atoms such as quinolinyl,
isoquinolinyl, benzimidazolyl, quinoxalinyl, quinazolinyl,
indolyl, indazolyl, and the like.

The term cycloalkyl as used herein means $C_3$ to $C_7$
saturated monocyclic hydrocarbon residues and thus
includes cyclopropyl, cyclobutyl, cyclopentyl, cyclohexyl
and cycloheptyl.

The term alkylene as used herein means branched or unbranched divalent saturated radicals of from one to about five carbon atoms which can have their free valences on the same of different carbon atom and thus includes methylene, 1,2-ethylene, 1,3-propylene, 1,4-butylene, 1,5-pentylene, and the like.

The synthesis of the compounds of the invention may be outlined as shown in Scheme A:

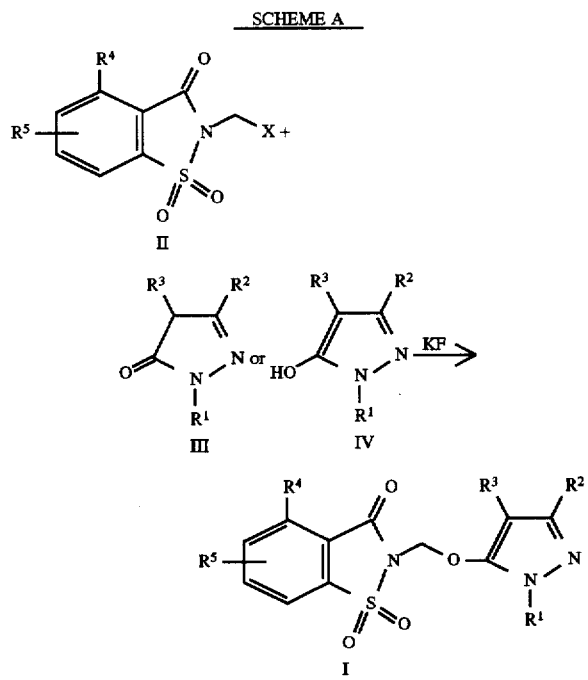

A suitably substituted 2-halomethyl-1,2-benzisothiazol-3 (2H)-one 1,1-dioxide of the formula II, wherein X is a halogen, preferably chlorine or bromine, in an appropriate organic solvent, such as dimethylformamide, is treated with an excess of potassium fluoride and at least one mole of a suitably substituted 2,4-dihydro-3H-pyrazol-3-one derivative of the formula III, or at least one mole of a suitably substituted pyrazole derivative of the formula IV, at a temperature in the range of about room temperature up to the boiling point of the solvent used, preferably at about room temperature, to afford the compounds of the formula I.

Alternatively, the compounds of the formula I can be prepared as illustrated in Scheme B.

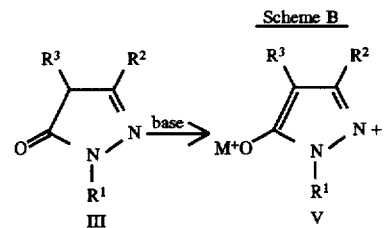

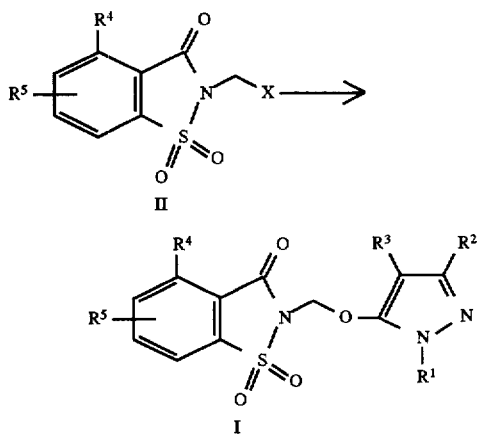

An excess of a suitably substituted 2,4-dihydro-3H-pyrazol-3-one derivative of the formula III is treated with a suitable alkali metal carbonate, preferably cesium carbonate, in an appropriate lower-alkanol solvent, such as methanol, at a temperature of about room temperature, to afford the suitably substituted pyrazole derivatives of the formula V, wherein $M^+$ is an alkali metal, preferably cesium (alternatively, the pyrazole derivative of the formula V can be prepared directly from the pyrazole derivatives of the formula IV by treatment of the latter with an alkali metal carbonate in a lower-alkanol solvent). The suitably substituted pyrazole derivative of the formula V can then be treated with a suitably substituted 2-halomethyl-1,2-benzisothiazol-3(2H)-one 1,1-dioxide of the formula II, wherein X is a halogen, preferably chlorine or bromine, in an appropriate organic solvent, such as dimethylformamide, at a temperature in the range of about 0° C. up to the boiling point of the solvent used, preferably at about room temperature, to afford the compounds of the formula I.

Simple chemical transformations which are conventional and well known to those skilled in the art of chemistry can be used for effecting changes in the functional groups of the compounds of the formula I. For example, the coupling of alcohols in the presence of triphenylphosphine/ diethylazodicarboxylate to afford the corresponding ether derivatives, the hydrolysis of esters to afford the corresponding acids, the dealkylation of aryl ethers to afford the corresponding phenol derivatives, catalytic debenzylation of benzyl esters to afford the corresponding acid derivatives, and the treatment of acids with isobutyl chloroformate and an appropriate amine derivative to afford the corresponding amide derivatives.

The compounds of Formula I are useful both in the free base form, and in the form of acid-addition salts, and both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts.

However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

Likewise, the compounds of the formula I which contain acidic functions, e.g. carboxylic acids, are useful both in the free acid form and in the form of base-addition salts and both forms are within the purview of the invention. The base-addition salts are often a more convenient form for use; and in practice, use of the salt form inherently amounts to use of the free acid form. The bases which can be used to prepare the base-addition salts include preferably those which produce, when combined with the free acid, pharmaceutically-acceptable salts, that is, salts whose cations are relatively innocuous to the animal organism in pharmaceutical doses of the salts, so that the beneficial properties inherent in the free acid are not vitiated by side effects ascribable to the cations. The base-addition salts can be prepared by the reaction of the free acid with a base, such as alkali metal or ammonium hydroxides or organic bases such as alkyl, dialkyl, or trialkylamines. If desired, the free acids can be regenerated from the base-addition salts by treatment of the salts with an appropriate aqueous acid.

The appropriately substituted 2-halomethyl-1,2-benzisothiazol-3(2H)-one 1,1-dioxides of the formula II can be prepared by procedures known in the art (see, for example, U.S. Pat. No. 5,128,339, issued Jul. 7, 1992, U.S. Pat. No. 5,236,917, issued Aug. 17, 1993, U.S. Pat. No. 5,250,696, issued Oct. 5, 1993, and U.S. Pat. No. 5,306,818, issued Apr. 26, 1994, the entire contents of each of which is incorporated herein by reference) or they can be prepared by the procedures described hereinbelow in the examples. The suitably substituted 2,4-dihydro-3H-pyrazol-3-one derivatives of the formula III and the suitably substituted pyrazole derivatives of the formulas IV and V are either commercially available, or they can be prepared by procedures known in the art or by the procedures described hereinbelow in the examples.

The structures of the compounds of the invention were established by the mode of synthesis, and by one or more of elemental analysis, and infrared, nuclear magnetic resonance and mass spectroscopy. The course of the reactions and the identity and homogenity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected.

EXAMPLE 1

To a solution of 2,4-dihydro-2,5-dimethyl-3H-pyrazol-3-one (475 mg; 4.24 mmol) in DMF (25 ml) was added 280 mg (4.83 mmol) of KF followed by 2-chloromethyl-4-isopropyl-6-methoxy-1,2-benzisothiazol-3(2H)-one 1,1-dioxide (1 g, 3.3 mmol), and the resulting mixture was stirred at room temperature for 24 hours and then was poured into ice/water. The above mixture was extracted with ethyl acetate and the organic layer was washed with water, dried, and concentrated in vacuo. The residue was purified by flash chromatography to afford 0.46 g (37%) of 4-isopropyl-6-methoxy-2-(1,3-dimethylpyrazol-5-yl-oxymethyl)-1,2-benzisothiazol-3(2H)-one 1,1-dioxide (Formula I: $R^1=R^2=CH_3$; $R^3=H$; $R^4=CH(CH_3)_2$; $R^5=6-OCH_3$) as a white solid, m.p. 146°–147° C.

EXAMPLE 2

(a)

To a mixture of 17.3 ml of ethyl benzoylacetate and 10 ml of water heated to 500° C. was added dropwise 5.3 ml of methyl-hydrazine over a period of 10 minutes (temperature rose to 70° C.) and the resulting mixture was heated at 60° C. for 2 hours. After adding 10 ml of dioxane the mixture was stirred at 55°–65° C. overnight, filtered, and the white solid was washed with water and dried in vacuo ($P_2O_5$) to afford 13.23 g of 2,4-dihydro-2-methyl-5-phenyl-3H-pyrazol-3-one (Formula III: $R^1=CH_3$; $R^2=Ph$; $R^3=H$) as a white solid, m.p. 207° C.(d)

(b)

To a solution of 2,4-dihydro-2-methyl-5-phenyl-3H-pyrazol-3-one (0.63 g; 3.62 mmol) in DMF (20 ml) was added 230 mg (3.96 mmol) of KF followed by 2-chloromethyl-4-isopropyl-6-methoxy-1,2-benzisothiazol-3(2H)-one 1,1-dioxide (1 g, 3.29 mmol) and the resulting mixture was stirred at room temperature for 24 hours and then poured into water. The above mixture was extracted with ethyl acetate and the organic layer was washed with water, brine, dried, and concentrated in vacuo. The residue was purified by flash chromatography to afford 0.4 g (27%) of 4-isopropyl-6-methoxy-2-(1-methyl-3-phenylpyrazol-5-yl-oxymethyl)-1,2-benzisothiazol-3(2H)-one 1,1-dioxide (Formula I: $R^1=CH_3$; $R^2=Ph$; $R^3=H$; $R^4=CH(CH_3)_2$; $R^5=6-OCH_3$) as a white solid, m.p. 126°–128° C.

EXAMPLE 3

To a solution of 2,4-dihydro-2-phenyl-5-trifluoromethyl-3H-pyrazol-3-one (Formula III: $R^1=Ph$; $R^2=CF_3$; $R^3=H$) (1.12 g; 4.91 mmol) in DMF (25 ml) was added 280 mg (4.83 mmol) of KF followed by 2-chloromethyl-4-isopropyl-6-methoxy-1,2-benzisothiazol-3(2H)-one 1,1-dioxide (1 g, 3.3 mmol) and the resulting mixture was stirred at room temperature for 24 hours and then was poured into water. The above mixture was extracted with ethyl acetate and the organic layer was washed with water, dried, and concentrated in vacuo. The residue was purified by flash chromatography to afford 0.29 g (18%) of 4-isopropyl-6-methoxy-2-(1-phenyl-3-trifluoromethylpyrazol-5-yl-oxymethyl)-1,2-benzisothiazol-3(2H)-one 1,1-dioxide (Formula I: $R^1=Ph$; $R^2=CF_3$; $R^3=H$; $R^4=CH(CH_3)_2$; $R^5=6-OCH_3$) as a solid

EXAMPLE 4

(a)

To a mixture of 12.7 ml (99.7 mmol) of ethyl acetoacetate and 10 ml of water heated to 52° C. was added dropwise 9.8 ml (99.7 mmol) of phenylhydrazine over a period of 30 minutes (temperature rose to 70° C.) and the resulting mixture was heated at 55°–60° C. for 1.5 hours. After adding 10 ml of dioxane the mixture was extracted with 100 ml of methylene chloride, the aqueous layer was treated with brine, and then was extracted with methylene chloride (2×). The combined organic layers were washed with brine, dried over sodium sulfate, filtered, and concentrated in vacuo. The residue was crystallized from ethyl acetate/hexane to afford 11.17 g (64%) of 2,4-dihydro-2-phenyl-5-methyl-3H-pyrazol-3-one (Formula III: $R^1$=Ph; $R^2$=$CH_3$; $R^3$=H) as a white solid, m.p. 125°–127° C.

(b)

To a mixture of 460 mg (7.9 mmol) of KF in DMF (25 ml) was added under nitrogen at room temperature 2,4-dihydro-2-phenyl-5-methyl-3H-pyrazol-3-one (1.38 g; 7.98 mmol) with stirring (5 minutes) followed by 2-chloromethyl-4-isopropyl-6-methoxy-1,2-benzisothiazol-3(2H)-one 1,1-dioxide (1.1 g, 3.63 mmol) and the resulting mixture was stirred at room temperature for 6 hours and then poured into water/ethyl acetate. The above mixture was extracted with ethyl acetate (3×75 ml) and the organic layer was dried over magnesium sulfate, and concentrated in vacuo. The residue (yellow foam, 1.3 g) was purified by flash chromatography (silica gel; 10–20% ethyl acetate in hexane) to afford 120 mg of 4-isopropyl-6-methoxy-2-(1-phenyl-3-methylpyrazol-5-yl-oxymethyl)-1,2-benzisothiazol-3(2H)-one 1,1-dioxide (Formula I: $R^1$=Ph; $R^2$=$CH_3$; $R^3$=H; $R^4$=CH($CH_3$)$_2$; $R^5$=6-$OCH_3$) as a white foam, m.p. 65°–670° C.

EXAMPLE 5

(a)

To a mixture of 4-isopropyl-6-methoxy-1,2-benzisothiazol-3(2H)-one 1,1-dioxide in acetic acid (20 ml) was added paraformaldehyde (0.7 g, 23.33 mmol), followed by 48% HBr in acetic acid (4.2 ml, 23.45 mmol). The mixture was heated at 50°–55° C. for 4 hours, cooled, poured over ice-water and filtered. The product was purified by column chromatography on silica gel eluting with 10–15% ethyl acetate/hexane to afford 1.88 g (66%) of 2-bromomethyl-4-isopropyl-6-methoxy-1,2-benzisothiazol-3(2H)-one 1,1-dioxide, m.p. 157°–159° C.

Alternatively, 2-bromomethyl-4-isopropyl-6-methoxy-1,2-benzisothiazol-3(2H)-one 1,1-dioxide was prepared as follows:

To a suspension of 4-isopropyl-6-methoxy-1,2-benzisothiazol-3(2H)-one 1,1-dioxide (1.020 kg, 4.2 mol) in 6 L of acetonitrile was added diisopropylethylamine (543 g, 4.2 mol) and the reaction mixture was stirred at ambient temperature for 30 minutes. At the end of this period, chloromethyl pivalate (633 g, 4.2 mol) was added in one portion and the resulting solution was refluxed on a steam bath for 20 hours. The acetonitrile was removed under vacuum and the residue was stirred with 6 L of water for 30 minutes. The off-white solid was collected by filtration, washed first with 6 L of water, followed by 3 L of hexane. The product was dried at 70° C. under vaccum for 18 hours to give 1.33 kg (91%) of 2-(pivaloyloxymethyl)-4-isopropyl-6-methoxy-1,2-benzisothiazol-3(2H)-one 1,1-dioxide, m.p. 178°–179° C.

A solution of 2-(pivaloyloxymethyl)-4-isopropyl-6-methoxy-1,2-benzisothiazol-3(2H)-one 1,1-dioxide (1.33 kg, 3.62 mol), 48% HBr in acetic acid (1 L) and 3 L of acetic acid was stirred on a steam bath (90°–95° C.) for 1.5 hours. The solvent (acetic acid) was removed under vacuum to give a thick slurry of an off-white residue which was diluted with 10 L of cold water and stirred for 30 minutes. The crude product was collected by filtration, washed first with 6 L of water and then with 3 L of saturated sodium bicarbonate solution. The crude solid was dried at 60°–70° C. for 20 hours and then was recrystallized from a mixture of 5 L of ethyl acetate and 6 L of hexane. Two crops were collected to give 1.16 kg (92%) of 2-bromomethyl-4-isopropyl-6-methoxy-1,2-benzisothiazol-3(2H)-one 1,1-dioxide, as an off-white solid, m.p. 157°–159° C.

Alternatively, the latter two step reaction sequence can be performed in a single step as follows:

A mixture 4-isopropyl-6-methoxy-1,2-benzisothiazol-3(2H)-one 1,1-dioxide (0.51 g, 2 mmol), acetonitrile (5.0 ml), chloromethyl pivalate (0.32 ml, 2.2 mmol) and diisopropylethylamine (0.42 ml, 2.4 mmol) was heated to reflux until the starting material was consumed and then 33% HBr/acetic acid (2.4 g, 10 mmol) was added and the mixture was refluxed for 15 minutes. The reaction mixture was coooled, quenched with ice-water and filtered to afford 0.42 g (65%) of 2-bromomethyl-4-isopropyl-6-methoxy-1,2-benzisothiazol-3(2H)-one 1,1-dioxide, m.p. 158°–160.5° C., after recrystallization from ethyl acetate/hexane (3/2).

(b)

A mixture 2,4-dihydro-2,5-diphenyl-3H-pyrazol-3-one (Formula III: $R^1$=$R^2$=Ph; $R^3$=H) (651 mg; 2.76 mmol) and $Cs_2CO_3$ (450 mg; 1.38 mmol) in methanol (12 ml) was stirred at 20° C. for 5 hours. The solvent was concentrated in vacuo, and the residue was dried in vacuo overnight. To a solution of the above residue in 12 ml of DMF was added 2-bromomethyl-4-isopropyl-6-methoxy-1,2-benzisothiazol-3(2H)-one 1,1-dioxide (800 mg, 2.3 mmol) and the resulting mixture was stirred at room temperature (20° C.) for 21 hours and then poured into water. The above mixture was extracted with ether (3×) and the organic layer was dried over sodium sulfate, and concentrated in vacuo. The residue (yellow foam, 854 mg, 74%) was purified by flash column chromatography (silica gel; 18–50% ethyl acetate in hexane) and by recrystallization from ethyl acetate/hexane to afford 609 mg of 4-isopropyl-6-methoxy-2-(1,3-diphenylpyrazol-5-yl-oxymethyl)-1,2-benzisothiazol-3(2H)-one 1,1-dioxide (Formula I: $R^1$=$R^2$=Ph; $R^3$=H; $R^4$=CH($CH_3$)$_2$; $R^5$=6-$OCH_3$) as a white foam, m.p. 62°–76° C.

EXAMPLE 6

(a)

Diethyl ethoxymethylene-malonate (5.20 ml; 26 mmol) was added rapidly to 2.75 ml (28 mmol) of phenylhydrazine in 15 ml of methanol and the resulting mixture was refluxed for 4 hours. The mixture was cooled and concentrated in vacuo, and the residue was crystallized from ethanol to afford 5.82 g (97%) of 2,4-dihydro-2-phenyl-4-ethoxycarbonyl-3H-pyrazol-3-one (Formula III: $R^1$=Ph; $R^2$=H; $R^3$=C(O)OEt) as white needles, m.p. 106°–107° C.

(b)

To a mixture of 2,4-dihydro-2-phenyl-4-ethoxycarbonyl-3H-pyrazol-3-one (5.8 g; 25 mmol) in 16 ml of ethanol/water (1:1) 4 g of KOH was added and the resulting mixture was heated at reflux for 4 hours. The mixture was cooled in an ice/bath, conc. HCl solution was added (until pH=1–2), and the resulting mixture was refluxed overnight. The reaction mixture was cooled, concentrated in vacuo, and the residue was dissolved in water. The aqueous layer was extracted with ethyl acetate (2×), the combined organic layer was dried over magnesium sulfate and concentrated in vacuo. The residual yellow oil was purified by silica gel column chromatography (25–30% ethyl acetate/hexane) to afford 1.5 g (38%) of 2,4-dihydro-2-phenyl-3H-pyrazol-3-one (Formula III: $R^1$=Ph; $R^2$=H; $R^3$=H) as a solid, m.p. 113°–114° C.

(c)

To a mixture of 2,4-dihydro-2-phenyl-3H-pyrazol-3-one (378 mg; 2.36 mmol) in DMF (6 ml) was added under nitrogen at room temperature 249 mg (4.3 mmol) of KF with stirring followed by 2-bromomethyl-4-isopropyl-6-methoxy-1,2-benzisothiazol-3(2H)-one 1,1-dioxide (750 mg, 2.15 mmol). The resulting mixture was stirred at room temperature for 2 hours and then quenched with saturated ammonium chloride solution. The above mixture was extracted with ether (3×30 ml) and the organic layer was dried over magnesium sulfate, and concentrated in vacuo. The residue (yellow solid) was purified by flash chromatography (silica gel; 5% ethyl acetate in methylene chloride) to afford 280 mg (31%) of 4-isopropyl-6-methoxy-2-(1-phenylpyrazol-5-yl-oxymethyl)-1,2-benzisothiazol-3(2H)-one 1,1-dioxide (Formula I: $R^1$=Ph; $R^2$=$R^3$=H; $R^4$=CH($CH_3$)$_2$; $R^5$'6-OCH$_3$) as a white solid, m.p. 118°–1190° C.

EXAMPLE 7

A mixture of 2,4-dihydro-2-(p-nitrophenyl)-5-methyl-3H-pyrazol-3-one (Formula III: $R^1$=4-$NO_2$Ph; $R^2$=$CH_3$; $R^3$=H) (664 mg; 3.03 mmol) and $Cs_2CO_3$ (494 mg; 1.52 mmol) in methanol (15 ml) was stirred at 20° C. for 5 hours. The solvent was concentrated in vacuo, and the residue was dried in vacuo overnight. To a solution of the above residue in 12 ml of DMF was added 2-bromomethyl-4-isopropyl-6-methoxy-1,2-benzisothiazol-3(2H)-one 1,1-dioxide (880 mg, 2.53 mmol) and the resulting mixture was stirred at room temperature (20° C.) for 4 hours and then was poured into water. The above mixture was extracted with ether (3×) and the organic layer was dried over sodium sulfate, and concentrated in vacuo. The residue (yellow solid) was purified by column chromatography (silica gel; 18–50% ethyl acetate in hexane) to afford 133 mg (11%) of 4-isopropyl-6-methoxy-2-[1-(p-nitrophenyl)-3-methylpyrazol-5-yl-oxy methyl]-1,2-benzisothiazol-3(2H)-one 1,1-dioxide (Formula I: $R^1$=4-$NO_2$-Ph; $R^2$=$CH_3$; $R^3$=H; $R^4$=CH($CH_3$)$_2$; $R^5$=6-$OCH_3$) as a white solid, m.p. 196°–198° C.

EXAMPLE 8

(a)

A mixture of 10 g (54.3 mmol) of ethyl trifluoroacetoacetate and 9.72 g (54.3 mmol) of 4-chlorophenylhydrazine and 1 mL of concentrated HCl in 130 ml of methanol was refluxed with stirring for 22 hours. After adding activated charcoal with stirring, the hot mixture was filtered, diluted with water, and the resulting white solid was filtered. The solid was washed with hexane and dried to afford 19 g of 2,4-dihydro-2-(4-chlorophenyl)-5-trifluoromethyl-3H-2-pyrazol-3-one (Formula III: $R^1$=4-Cl—Ph; $R^2$=$CF_3$; $R^3$=H) as a white solid.

(b)

A mixture 2,4-dihydro-2-(4-chlorophenyl)-5-trifluoromethyl-3H-2-pyrazol-3-one (408 mg; 1.55 mmol) and $Cs_2CO_3$ (252 mg; 0.774 mmol) in methanol (8 ml) was stirred at 20° C. for 5 hours. The solvent was concentrated in vacuo, and the residue was dried in vacuo overnight. To a solution of the above residue in 6 ml of DMF was added 2-bromomethyl-4-isopropyl-6-methoxy-1,2-benzisothiazol-3(2H)-one 1,1-dioxide (450 mg, 1.29 mmol) and the resulting mixture was stirred at room temperature (20° C.) overnight and poured into water. The above mixture was extracted with ether (3×) and the organic layer was dried over sodium sulfate, and concentrated in vacuo. The residue was purified by column chromatography (silica gel; 12–50% ethyl acetate in hexane) and recrystallized from methylene chloride/hexane to afford 498 mg (73%) of 4-isopropyl-6-methoxy-2-[1-(4-chlorophenyl)-3-trifluoromethylpyrazol-5-yl-oxymethyl]-1,2-benzisothiazol-3(2H)-one 1,1-dioxide (Formula I: $R^1$=4-Cl—Ph; $R^2$=$CF_3$; $R^3$=H; $R^4$=CH($CH_3$)$_2$; $R^5$=6-$OCH_3$) as a white solid, m.p. 160°–161° C.

EXAMPLE 9

To a solution of 1-phenyl-3-trifluoromethyl-5-hydroxypyrazole (1.57 g; 6.9 mmol) in 40 ml of methanol was added $Cs_2CO_3$ (1.12 g; 3.44 mmol) in methanol (8 ml) and the mixture was stirred at room temperature for 2 hours. The solvent was concentrated in vacuo, and the residue was dried in vacuo overnight. To a solution of the above residue in 30 ml of DMF was added 2-chloromethyl-4-isopropyl-6-hydroxy-1,2-benzisothiazol-3(2H)-one 1,1-dioxide (1 g, 3.45 mmol) and the resulting mixture was stirred at room temperature (20° C.) overnight and then poured into ice/water. The above mixture was extracted with ether/ethyl acetate (1:1, 3×250 ml) and the organic layer was washed with water, brine, dried over sodium sulfate, and concentrated in vacuo. The residue was purified by flash column chromatography (silica gel; 5% ethyl acetate in chloroform) to afford 1 g (60%) of 4-iso-ropyl-6-hydroxy-2-(1-phenyl-3-trifluoro methylpyrazol-5-yl-oxymethyl)-1,2-benzisothiazol-3(2H)-one 1,1-dioxide (Formula I: $R^1$=Ph; $R^2$=$CF_3$; $R^3$=H; $R^4$=CH($CH_3$)$_2$; $R^5$=6-OH) as a white solid, m.p. 178°–180° C.

EXAMPLE 10

(a)

A mixture of 1.32 ml (9.1 mmol) of ethyl trifluoroacetoacetate, 1 g (9.1 mmol) of 2-hydrazinopyridine, and 0.6 ml of conc. HCl in 10 ml of methanol was refluxed with stirring for 1.5 hours. After adding activated charcoal the mixture was stirred for 1 hour, filtered, and the solid was washed with hot methanol and the filtrate was concentrated in vacuo. The residue was triturated in cold water, the resulting white solid was filtered, and the filtrate was extracted with ethyl acetate (3×). The combined organic layer and the above solid were dissolved in ethyl acetate, dried over magnesium sulfate, and concentrated in vacuo to afford 1.5 g of a white solid product. The white solid was dissolved in toluene and the solution was refluxed under nitrogen for 3 days. The resulting solution was concentrated in vacuo, and the residue was recrystallized from hexane to afford 1.1 g (54%) of 2,4-dihydro-2-(2-pyridyl)-5-trifluoromethyl-3H-pyrazol-3-one (Formula III: $R^1$=2-pyridyl; $R^2$=$CF_3$; $R^3$=H) as a white solid, m.p. 76–77° C.

(b)

To a mixture of 2,4-dihydro-2-(2-pyridyl)-5-trifluoromethyl-3H-2-pyrazol-3-one (292 mg; 1.27 mmol) in DMF (8 ml) was added 136 mg (2.34 mmol) of KF at room temperature under nitrogen, and the mixture was stirred for 10 minutes. To the above solution was added 2-bromomethyl-4-isopropyl-6-methoxy-1,2-benzisothiazol-3(2H)-one 1,1-dioxide (400 mg, 1.14 mmol) and the resulting mixture was stirred at room temperature (20° C.) for 1 hour. The above mixture was quenched with saturated ammonium chloride, extracted with ether (3×) and the organic layer was dried over magnesium sulfate, and concentrated in vacuo. The residue was purified by column chromatography (silica gel; 20% ethyl acetate in hexane) to afford 443 mg (77%) of 4-isopropyl-6-methoxy-2-[1-(2-pyridyl)-3-trifluoromethylpyrazol-5-yl-oxymethyl]-1,2-benzisothiazol-3(2H)-one 1,1-dioxide (Formula I: $R^1$=2-pyridyl; $R^2$=$CF_3$; $R^3$=H; $R^4$=$CH(CH_3)_2$; $R^5$=6-$OCH_3$) as a white solid, m.p. 132°–133° C.

EXAMPLE 11

(a)

A mixture of 5 g (27.2 mmol) of ethyl trifluoroacetoacetate and 4.16 g (27.2 mmol) of 4-nitrophenylhydrazine and 0.6 mL of concentrated HCl in 100 ml of methanol was refluxed with stirring for 22 hours. After adding activated charcoal with stirring, the hot mixture was filtered, the filtrate was concentrated in vacuo, and the residue was diluted with water. The mixture was extracted with methylene chloride, the organic layer was dried and concentrated in vacuo, and the residue was recrystallized from methylene chloride/hexane to yield 4.33 g of a powder. The solid was purified by column chromatography (silica gel; 50–85% ethyl acetate in hexane) to afford ethyl trifluoroacetoacetate 4-nitrophenylhydrazone as a white solid.

(b)

To a mixture of 382 mg (1.2 mmol) of ethyl trifluoroacetoacetate 4-nitrophenylhydrazone in 10 ml of THF was added 53 mg (60%; 1.32 mmol) of NaH and the resulting mixture was stirred at room temperature for 4 hours and at 50° C. for 16 hours. The reaction mixture was quenched with ammonium chloride solution, the aqueous layer was extracted with ethyl acetate (3×), and the combined organic layer was dried and concentrated in vacuo. The residue was purified by column chromatography (silica gel; 50% ethyl acetate in hexane) and recrystallized from methylene chloride/hexane to afford 1-(4-nitrophenyl)-3-trifluoromethyl-5-hydroxypyrazole as a white solid.

(c)

A mixture of 1-(4-nitrophenyl)-3-trifluoromethyl-5-hydroxypyrazole (450 mg; 1.65 mmol) and $Cs_2CO_3$ (269 mg; 0.825 mmol) in methanol (9 ml) was stirred at 20° C. for 4 hours. The solvent was concentrated in vacuo, and the residue was dried in vacuo overnight. To a solution of the above residue in 7 ml of DMF was added 2-bromomethyl-4-isopropyl-6-methoxy-1,2-benzisothiazol-3(2H)-one 1,1-dioxide (479 mg, 1.37 mmol) and the resulting mixture was stirred at room temperature (20° C.) for 3 hours and then poured into water. The above mixture was extracted with ether (3×) and the organic layer was dried over sodium sulfate, and concentrated in vacuo. The residue was purified by column chromatography (silica gel; 18–33% ethyl acetate in hexane) and recrystallized from methylene chloride/hexane to afford 350 mg (47%) of 4-isopropyl-6-methoxy-2-[1-(4-nitrophenyl)-3-trifluoromethylpyrazol-5-yl-oxymethyl]-1,2-benzisothiazol-3(2H)-one 1,1-dioxide (Formula I: $R^1$=4-$NO_2$—Ph; $R^2$=$CF_3$; $R^3$=H; $R^4$=$CH(CH_3)_2$; $R^5$=6-$OCH_3$) as a white solid, m.p. 185°–187° C.

EXAMPLE 12

To a mixture of 2,4-dihydro-2-phenyl-5-ethoxycarbonyl-3H-pyrazol-3-one (Formula III: $R^1$=Ph; $R^2$=C(O)OEt; $R^3$=H) (1.2 g; 5.1 mmol) in DMF (15 ml) was added 500 mg (9 mmol) of KF at room temperature under nitrogen, and the mixture was stirred for 10 minutes. To the above solution was added 2-bromomethyl-4-isopropyl-6-methoxy-1,2-benzisothiazol-3(2H)-one 1,1-dioxide (1.6 g, 4.5 mmol) and the resulting mixture was stirred at room temperature (20° C.) for 1 hour. The above mixture was quenched with a saturated ammonium chloride solution, extracted with ether (3×), and the organic layer was washed with water, dried over magnesium sulfate, and concentrated in vacuo. The residue was purified by column chromatography (silica gel; 20% ethyl acetate in hexane) to afford 1 g (45%) of 4-isopropyl-6-methoxy-2-(1-phenyl-3-ethoxy carbonylpyrazol-5-yl-oxymethyl)-1,2-benzisothiazol-3(2H)-one 1,1-dioxide (Formula I: $R^1$=Ph; $R^2$=C(O)OEt; $R^3$=H; $R^4$=$CH(CH_3)_2$; $R^5$=6-$OCH_3$) as a white solid, m.p. 170°–171° C.

EXAMPLE 13

To a solution of 4-isopropyl-6-hydroxy-2-(1-phenyl-3-trifluoromethylpyrazol-5-yl-oxymethyl)-1,2-benzisothiazol-3(2H)- one 1,1-dioxide (940 mg ; 1.95 mmol), 540 mg (2.05 mmol) of $(Ph)_3P$, and 5-dimethylaminomethyl-2-hydroxymethylfuran (320 mg; 2.05 mmol) in 30 ml of THF was added with cooling 360 mg (2.06 mmol) of diethylazodicarboxylate (DEAD) and the resulting mixture was allowed to stir overnight at room temperature. The mixture was concentrated in vacuo and the residue was purified by flash column chromatography (silica gel; ethyl acetate) to afford 0.4 g (33%) of 4-isopropyl-6-[1-(5-dimethylaminomethyl-2-furanyl methoxy]-2-(1-phenyl-3-trifluoromethylpyrazol-5-yl-oxymethyl]-1,2-benzisothiazol-3(2H)-one 1,1-dioxide (Formula I: $R^1$=Ph; $R^2$=$CF_3$; $R^3$=H; $R^4$=$CH(CH_3)2$; $R^5$=6-[1-(5-dimethylaminomethyl-2-furanyl)methoxy]) as a gum.

EXAMPLE 14

(a)

To a suspension of sodium hydride (4.24 g, 106 mmol; 60% dispersion in mineral oil washed with ether) in 28 ml of ether was added with vigorous stirring 5 g (110 mmol) of ethanol at such a rate to cause a gentle reflux. A mixture of dry ethyl acetate (12.9 ml, 132 mmol) and ethyl isonicotinate (10 g, 66.2 mmol) was added to the above reaction mixture in one portion, and the resulting mixture was refluxed for 18 hours and cooled. The mixture was diluted with water (100 ml), stirred, and washed with ether (2×). The aqueous layer was acidified with acetic acid, and the organic layer was separated. The aqueous layer was extracted with methylene chloride, the combined organic layer was dried over sodium sulfate and concentrated in vacuo. The resulting residue was recrystallized from methylene chloride/hexane to afford 9.5 g (74%) of ethyl 4-(pyridyl)carbonylacetate.

(b)

A mixture of 1.5 g (7.8 mmol) of ethyl 4-(pyridyl) carbonylacetate, 4-chlorophenylhydrazine (1.4 g; 7.8 mmol), and 0.2 ml of conc. HCl in 18 ml of methanol was stirred at 60° C. for 20 hours, cooled and diluted with water. The yellow solid precipitate was filtered, dissolved in toluene, and the solution was stirred at 110° C. for 19 hours and cooled. The mixture was diluted with sodium bicarbonate solution, extracted with ethyl acetate (4×), the combined organic layer was dried over sodium sulfate, and concentrated in vacuo. The solid residue was recrystallized from acetonitrile to afford 789 mg (37%) of 1-(4-chlorophenyl)-3-(4-pyridyl)-5-hydroxypyrazole, which was purified by column chromatography (silica gel; ethyl acetate/hexane; methylene chloride/acetone,and methylene chloride/methanol).

(c)

A mixture of 1-(4-chlorophenyl)-3-(4-pyridyl)-5-hydroxy pyrazole (406 mg; 1.49 mmol) and $Cs_2CO_3$ (243 mg; 0.75 mmol) in methanol (8 ml) was stirred at room temperature for 4 hours. The solvent was concentrated in vacuo, and the residue was dried in vacuo overnight. To the above residue was added 7 ml of DMF and 2-bromomethyl-4-isopropyl-6-methoxy-1,2-benzisothiazol-3(2H)-one 1,1-dioxide (519 mg, 1.49 mmol) and the resulting mixture was stirred at room temperature for 5 hours and poured into water. The above mixture was extracted with methylene chloride (3×), the organic layer was dried over sodium sulfate, and concentrated in vacuo. The residue was purified by column chromatography (silica gel; 33–50% ethyl acetate/hexane; 12–50% methylene chloride/acetone) and recrystallized from methylene chloride/hexane to afford 401 mg (50%) of 4-isopropyl-6-methoxy-2-[1-(4-chlorophenyl)-3-(4-pyridyl) pyrazol-5-yl-oxymethyl]-1,2-benzisothiazol-3(2H)-one 1,1-dioxide (Formula I: $R^1$=4-Cl—Ph; $R^2$=4-pyridyl; $R^3$=H; $R^4$=$CH(CH_3)_2$; $R^5$=6-$OCH_3$) as a white solid. m.p. >190° C. (dec.).

EXAMPLE 15

(a)

A mixture of 5 g (27.2 mmol) of ethyl trifluoroacetoacetate, 4.76 g (27.2 mmol) of 4-methoxyphenylhydrazine hydrochloride, and 0.5 ml of conc. HCl in 60 ml of methanol was refluxed with stirring for 22 hours. After removing methanol in vacuo, toluene was added and the resulting mixture was refluxed for 20 hours and cooled. The mixture was diluted with aqueous sodium bicarbonate solution, extracted with ethyl acetate, and the organic layer was dried over sodium sulfate and concentrated in vacuo. The residue was recrystallized from methylene chloride/hexane and ethyl acetate/hexane to afford 3.7 g (53%) of 1-(4-methoxyphenyl)-3-trifluoromethyl-5-hydroxypyrazole as a tan solid.

(b)

A mixture of 1-(4-methoxyphenyl)-3-trifluoromethyl-5-hydroxy pyrazole (489 mg; 1.89 mmol), 2-bromomethyl-4-isopropyl-6-methoxy-1,2-benzisothiazol-3(2H)-one 1,1-dioxide (600 mg, 1.72 mmol), and KF (200 mg; 3.44 mmol) in DMF (8 ml) was stirred at 20° C. for 2 hours and the mixture was diluted with water. The above mixture was extracted with ether (3×) and the organic layer was dried over sodium sulfate, and concentrated in vacuo. The residue was purified by column chromatography (silica gel; 25–50% ethyl acetate/hexane) and recrystallized from ethyl acetate/hexane to afford 418 mg (46%) of 4-isopropyl-6-methoxy-2-[1-(4-methoxyphenyl)-3-trifluoromethylpyrazol-5-yl-oxymethyl]-1,2-benzisothiazol-3(2H)-one 1,1-dioxide (Formula I: $R^1$=4-$CH_3O$—Ph; $R^2$=$CF_3$; $R^3$=H; $R^4$=$CH(CH_3)_2$; $R^5$=6-$OCH_3$) as a white solid, m.p. 111°–113° C.

EXAMPLE 16

(a)

A mixture of 2.28 g (10 mmol) of 1-phenyl-3-trifluoromethyl-5-hydroxypyrazole and 1.6 g (12 mmol) of N-chlorosuccinimide in 8 ml of 20% TFA/acetic acid and 32 mL of acetic acid was stirred at room temperature for 16 hours and diluted with ice/water with cooling. The white precipitate was filtered and purified by column chromatography (silica gel; 20–33% ethyl acetate/hexane) to afford 550 mg (21%) of 1-phenyl-3-trifluoromethyl-4-chloropyrazole as a solid.

(b)

A mixture 1-phenyl-3-trifluoromethyl-4-chloropyrazole (524 mg; 2 mmol), 2-bromomethyl-4-isopropyl-6-methoxy-1,2-benzisothiazol-3(2H)-one 1,1-dioxide (696 mg, 2 mmol), and KF (232 mg; 4 mmol) in DMF (8 ml) was stirred at 20° C. for 16 hours and the mixture was diluted with water. The above mixture was extracted with methylene chloride (3×) and the organic layer was dried over sodium sulfate, and concentrated in vacuo. The white residue was recrystallized from methylene chloride/hexane and purified by column chromatography (silica gel; 20% ethyl acetate/hexane; methylene chloride) to afford 730 mg (69%) of 4-isopropyl-6-methoxy-2-(1-phenyl-3-trifluoromethyl-4-chloropyrazol-5-yl-oxymethyl)-1,2-benzisothiazol- 3(2H)-one 1,1-dioxide (Formula I: $R^1$=Ph; $R^2$=$CF_3$; $R^3$=Cl; $R^4$=$CH(CH_3)_2$; $R^5$=6-$OCH_3$) as a white solid, m.p. 185°–1870° C.

EXAMPLE 17

(a)

To a solution of 4-isopropyl-6-hydroxy-2-(1-phenyl-3-trifluoromethylpyrazol-5-yl-oxymethyl)-1,2-benzisothiazol-3(2H)-one 1,1-dioxide (1 g; 2.08 mmol) in THF containing $(Ph)_3P$ (550 mg; 2.09 mmol) and DEAD (360 mg; 2.07 mmol) was added benzyl 4-hydroxybutyrate (410 mg;2.099 mmol) and the resulting mixture was stirred at room temperature for 15 hours. The mixture was concentrated in vacuo and the residue was purified by flash chromatography (silica gel) to afford 870 mg (64%) of 4-isopropyl-6-[3-(phenylmethyloxycarbonyl)propoxy]-2-(1-phenyl-3-trifluoro methylpyrazol-5-yl-oxymethyl)-1,2-benzisothiazol-3(2H)-one 1,1-dioxide (Formula I: $R^1$=Ph; $R^2$=$CH_3$; $R^3$=H; $R^4$=$CH(CH_3)_2$; $R^5$=6-$O(CH_2)_3CO_2CH_2Ph$) as a solid, m.p. 99°–101° C.

(b)

A mixture of 4-isopropyl-6-[3-(phenylmethyloxycarbonyl)propoxy]-2-(1-phenyl-3-trifluoromethylpyrazol-5-yl-oxymethyl)-1,2-benzisothiazol-3(2H)-one 1,1-dioxide (820 mg) and 200 mg of 10% Pd/C in 40 ml of ethyl acetate was hydrogenated (hydrogen balloon). The catalyst was removed on a pad of CELITTEO and the filtrate was concentrated in vacuo to afford 640 mg (90%) of 4-isopropyl-6-[3-(carboxy)propoxy] -2-(1-phenyl-3-trifluoromethylpyrazol-5-yl-oxymethyl)-1, 2-benzisothiazol-3(2H)-one 1,1-dioxide (Formula I: $R^1$=Ph; $R^2$=$CH_3$; $R^3$=H; $R^4$=$CH(CH_3)_2$; $R^5$=6-$O(CH_2)_3CO_2$as a foam.

EXAMPLE 18

(a)

To a solution of 4-isopropyl-6-hydroxy-2-(1-phenyl-3-trifluoromethylpyrazol-5-yl-oxymethyl)-1,2-benzisothiazol-3(2H)-one 1,1-dioxide (1 g; 2.08 mmol) in THF containing $(Ph)_3P$ (550 mg; 2.09 mmol) and DEAD (360 mg; 2.07 mmol) was added benzyl 2,2-dimethyl-3-

17 hydroxypropionate (440 mg;2.099 mmol) and the resulting mixture was stirred at room temperature for 15 hours. The mixture was concentrated in vacuo and the residue was purified by flash chromatography (silica gel) to afford 440 mg (32%) of 4-isopropyl- 6-[2-(phenylmethyloxycarbonyl-2-methyl)propoxy]-2-(1-phenyl-3-trifluoromethylpyrazol-5-yl-oxymethyl)-1,2-benzisothiazol-3(2H)-one 1,1-dioxide (Formula I: $R^1$=Ph; $R^2$=$CF_3$; $R^3$=H; $R^4$=$CH(CH_3)_2$; $R^5$=6-$OCH_2C(CH_3)_2CO_2CH_2Ph$) as a gum.

(b)

A mixture of 4-isopropyl-6-[2-(phenylmethyloxycarbonyl-2-methyl)-propoxy]-2-(1-phenyl-3-trifluoromethylpyrazol-5-yl-oxy methyl)-1,2-benzisothiazol-3(2H)-one 1,1-dioxide (440 mg) and 110 mg of 10% Pd/C in 30 ml of ethyl acetate was hydrogenated (hydrogen balloon). The catalyst was removed on a pad of CELITE® and the filtrate was concentrated in vacuo to afford 350 mg (92%) of 4-isopropyl-6-[2-(carboxy-2-methyl)propoxy]-2-(1-phenyl-3-trifluoromethylpyrazol-5-yl-oxymethyl)-1,2-benzisothiazol-3(2H)-one 1,1-dioxide (Formula I: $R^1$=Ph; $R^2$=$CF_3$; $R^3$=H; $R^4$=$CH(CH_3)_2$; $R^5$=6-$OCH_2C(CH_3)_2CO_2H$) as a foam.

EXAMPLE 19

(a)

To a solution of 20 g (125 mmol) of diethyl malonate in 80 ml of absolute ethanol was added with stirring a solution of KOH pellets (7 g) in 80 ml of absolute ethanol over a period of 12 minutes and the resulting mixture was stirred at room temperature for 2 hours. The solution was heated to boiling, filtered while hot, and the filtrate was cooled and filtered to afford, after drying, 11.14 g (53%) of potassium ethyl malonate. To a stirred and cooled (10° C.) mixture of the above potassium salt (11.14 g; 66 mmol) in 100 ml of acetonitrile was added triethylamine (6.5 g, 64 mmol) and magnesium chloride (7.5 g, 80 mmol) and the resulting mixture was stirred at room temperature for 2 hours. To the above mixture, cooled to 0° C., was added dropwise pentafluorobenzoyl chloride (7.4 g; 32 mmol) followed by the addition of 0.64 g of triethylamine, and the resulting mixture was allowed to stir at room temperature overnight and then was concentrated to dryness. The resulting mixture was diluted with 40 ml of toluene, concentrated in vacuo, and the residue was rediluted with 60 ml of toluene, stirred, and cooled to 10° C. An aqueous HCl solution (13%; 45 ml) was added in portions to the above reaction mixture at below 25° C., the organic layer was washed with 13% HCl solution (2×12 ml), water, and concentrated in vacuo. The residue was distilled to afford 8.4 g (93%) of ethyl pentafluorobenzoylacetate as an oil, b.p.139°–147° C.

(b)

A mixture of 2.82 g (10 mmol) of ethyl pentafluorobenzoylacetate, phenylhydrazine (1.08 g; 10 mmol), and 0.33 ml of conc. HCl in 10 ml of methanol was refluxed for 18 hours. The mixture was concentrated in vacuo, the residue was diluted with toluene and heated at 110° C. for 20 hours and cooled. The mixture was diluted with sodium bicarbonate solution and extracted with ethyl acetate (3×). The combined organic layer was dried over sodium sulfate and concentrated in vacuo. The residue was purified by column chromatography (silica gel; 20–50% ethyl acetate/hexane) and recrystallized from ethyl acetate/hexane to afford 1.76 g (54%) of 1-phenyl-3-(pentafluorophenyl)-5-hydroxypyrazole as a white solid, mp 149–151° C.

18

(c)

A mixture of 2-bromomethyl-4-isopropyl-6-methoxy-1,2-benzisothiazol-3(2H)-one 1,1-dioxide (550 mg, 1.58 mmol), 1-phenyl-3-(pentafluorophenyl)-5-hydroxypyrazole (567 mg; 1.7 mmol), and KF (183 mg; 3.16 mmol) in 7 ml of DMF was stirred at room temperature for 3 hours and the resulting mixture was diluted with water. The solid product was filtered, redissolved in methylene chloride (80 ml), and filtered and the filtrate was concentrated in vacuo. The residue was purified by column chromatography (silica gel; 20–100% methylene chloride/hexane) and recrystallized from methylene chloride/hexane to afford 578 mg (62%) of 4-isopropyl-6-methoxy-2-[1-phenyl-3-(pentafluorophenyl pyrazol-5-yl-oxymethyl]-1,2-benzisothiazol-3(2H)-one 1,1-dioxide (Formula I: $R^1$=Ph; $R^2$=pentafluorophenyl; $R^3$=H; $R^4$=$CH(CH_3)_2$; $R^5$=6-$OCH_3$) as a white solid, m.p. 160°–162° C.

EXAMPLE 20

(a)

3-Aminopyridine (8 g, 95 mmol) was dissolved in concentrated HCl (50 mL) and cooled to −5° C. A solution of sodium nitrite (6.6 g, 95 nmmol) in water was added dropwise while maintaining the temperature below 0° C. After ¾ of an hour the chilled solution was added dropwise to a solution of stannous chloride (4 g, 178 mmol) in conc. HCl (25 ml) at −5° C. After an additional hour the solid which formed was collected by filtration, placed in a beaker of ice and then treated with 50% KOH until the mixture was strongly basic. The mixture was extracted with methylene chloride and the organic solution was dried over magnesium sulfate, and concentrated in vacuo to afford 4.2 g (41%) of 3-pyridylhydrazine.

(b)

To a mixture of 1 g (9.1 mmol) of 3-pyridylhydrazine in 10 ml of methanol was added with stirring and under nitrogen ethyl trifluoroacetoacetate (1.32 ml; 9.1 mmol), and then 1 ml of conc. HCl was added and the resulting mixture was refluxed for 2 hours. The mixture was concentrated in vacuo, the residue was neutralized with cold sodium bicarbonate solution, and extracted with ethyl acetate (3×). The combined organic layer was dried over magnesium sulfate and concentrated in vacuo. The resulting residue (hydrazone) was diluted with toluene and heated at 110° C. overnight and cooled. The mixture was concentrated in vacuo and the residue was purified by column chromatography (silica gel; 5–15% methanol/methylene chloride) to afford 365 mg (19%) of 2,4-dihydro-2-(3-pyridyl)-5-trifluoromethyl-3H-pyrazol-3-one (Formula III: $R^1$=3-pyridyl; $R^2$=$CF_3$; $R^3$=H) as a yellow solid.

(c)

A mixture of 2,4-dihydro-2-(3-pyridyl)-5-trifluoromethyl-3H-pyrazol-3-one (292 mg; 1.28 mmol) and KF (136 mg; 2.32 mmol) in 15 ml of DMF was stirred under nitrogen at room temperature for 15 minutes and then 2-bromomethyl-4-isopropyl-6-methoxy-1,2-benzisothiazol-3(2H)-one 1,1-dioxide (400 mg, 1.16 mmol) was added. The reaction mixture was stirred at room temperature for 45 minutes and diluted with ice/water (150 ml). The mixture was extracted with ether (4×100 ml), the organic layer was filtered and concentrated in vacuo, and the solid residue (in methylene chloride) was purified by column chromatography (silica gel; 20–30% ethyl acetate/hexane) and triturated in ether to afford 400 mg (70%) of 4-isopropyl-6-methoxy-2-[1-(3-lpyridyl)-3-(trifluoromethyl) pyrazol-5-yl-oxymethyl]-1,2-benzisothiazol-3(2H)-one 1,1-dioxide (Formula I: $R^1$=3-pyridyl; $R^2$=$CF_3$; $R^3$=H; $R^4$=$CH(CH_3)_2$; $R^5$=6-$OCH_3$) as a white solid, m.p. 156°–157° C.

EXAMPLE 21

A mixture of 1 g (2 mmol) of 4-isopropyl-6-methoxy-2-[1-phenyl-3-(ethoxycarbonyl)pyrazol-5-yl-oxymethyl -1,2-benzisothiazol-3(2H)-one 1,1-dioxide, 18 ml of 20% sulfuric acid solution, and 30 ml of dioxane was refluxed for 15 hours, cooled, and then poured into water/ethyl acetate. The aqueous layer was extracted with ethyl acetate (3×), the combined organic layer was dried over magnesium sulfate, filtered, and concentrated in vacuo to afford 620 mg (66%) of the desired acid as a yellow solid. The solid product was triturated in ether and recrystallized from acetonitrile (2×) to afford 420 mg (45%) of 4-isopropyl-6-methoxy-2-[1-phenyl-3-(carboxy)pyrazol-5-yl-oxymethyl]-1,2-benzisothiazol-3(2H)-one 1,1-dioxide (Formula I: $R^1$=Ph; $R^2$=$CO_2H$; $R^3$=H; $R^4$=$CH(CH_3)_2$; $R^5$=6-$OCH_3$) as a solid, m.p. 193°–194.50° C.

EXAMPLE 22

(a)

A mixture of 3.6 ml (24 mmol) of ethyl trifluoroacetoacetate, 3.64 g (20 mmol) of 4-hydrazinopyridine, and 3.4 g (41 mmol) of sodium acetate in 20 ml of ethanol was refluxed under nitrogen with stirring for 15 hours. The mixture was diluted with water, filtered, and the resulting solid was washed with water, hexane, and dried in vacuo to yield 3.09 g (crop 1) of a solid mixture (mainly hydrazone). The filtrate was concentrated in vacuo to yield the second solid (251 mg) which was the desired product. The above hydrazone (3.09 g, crop 1) in 50 ml of toluene was refluxed overnight, filtered while hot, and the residual solid was crystallized from ethanol to yield 1 g of the desired cyclic product. The above mother liquor was concentrated in vacuo, the residual solid was refluxed in ethyl acetate, and the resulting solid was filtered to yield 1.32 g of additional desired product. The combined product (251 mg, 1 g, 1.32 g) was further dried at 50° C. in vacuo to afford 2.42 g (53%) of 1-(4-pyridyl)-3-trifluoromethyl-5-hydroxypyrazole as an amorphous solid, m.p. 270–280° C.(d).

(b)

To a mixture of 1-(4-pyridyl)-3-trifluoromethyl-5-hydroxypyrazole (316 mg; 1.36 mmol) in DMF (20 ml) was added 128 mg (2.24 mmol) of KF at room temperature under nitrogen, and the mixture was stirred for 20 minutes. To the above solution was added 2-bromomethyl-4-isopropyl-6-methoxy-1,2-benzisothiazol-3(2H)-one 1,1-dioxide (400 mg, 1.12 mmol) and the resulting mixture was stirred at room temperature for 45 minutes. The above mixture was quenched with ice/saturated ammonium chloride, extracted with ether (3×) and the organic layer was washed with water, dried over magnesium sulfate, and concentrated in vacuo. The residual yellow solid was purified by column chromatography (silica gel; 30–50% ethyl acetate in hexane) to afford 240 mg (43%) of 4-isopropyl-6-methoxy-2-[1-(4-pyridyl)-3-trifluoromethylpyrazol-5-yl-oxymethyl]-1,2-benzisothiazol-3(2H)-one 1,1-dioxide (Formula I: $R^1$=4-pyridyl; $R^2$=$CF_3$; $R^3$=H; $R^4$=$CH(CH_3)_2$; $R^5$=6-$OCH_3$) as a white solid, m.p. 161°–162° C.

EXAMPLE 23

(a)

A mixture of 2,4-dihydro-2-phenyl-5-ethoxycarbonyl-3H-pyrazol-3-one (10 g; 43 mmol) and 1-(2-aminoethyl)pyrrolidine (10 ml) was heated at 130° C. under nitrogen for 2 hours and cooled. The mixture was triturated in hexane, filtered and the solid was washed with hexane to yield 15 gm of a crude product. A portion (8.6 g ) of the crude product was purified by column chromatography (silica gel, triethylamine:methanol:methylene chloride 1:9:90) to afford 5.04 g of 2,4-dihydro-2-phenyl-5-[C(O)NH($CH_2$)$_2$-1-pyrrolidinyl]-3H-pyrazol-3-one (Formula III: $R^1$=Ph; $R^2$=C(O)NH($CH_2$)$_2$-1-pyrrolidinyl; $R^3$=H) as a tan solid, which was further crystallized in toluene/methanol (2×) to yield a white solid, m.p. 210°–211° C.

(b)

To a mixture of 2,4-dihydro-2-phenyl-5-[C(O)NH($CH_2$)$_2$-1-pyrrolidinyl]-3H-pyrazol-3-one (379 mg; 1.26 mmol) in methanol (40 ml) was added under nitrogen and with stirring $Cs_2CO_3$ (206 mg; 0.63 mmol). The mixture was stirred at room temperature for 2 hours, and then was concentrated in vacuo. The above residue was dried in vacuo overnight. To the above residue in 30 ml of DMF was added 2-bromomethyl-4-isopropyl-6-methoxy-1,2-benzisothiazol-3(2H)-one 1,1-dioxide (400 mg, 1.14 mmol) and the resulting mixture was stirred at room temperature for 15 minutes and then the reaction mixture was poured into ice/water. The aqueous layer was extracted with ethyl acetate (3×), the organic layer was washed with water (3×), dried over magnesium sulfate, and concentrated in vacuo to afford 439 mg of 4-isopropyl-6-methoxy-2-[1-phenyl-3-(C(O)NH($CH_2$)$_2$-1-pyrrolidinyl)pyrazol-5-yl-oxymethyl]-1,2-benzisothiazol-3(2H)-one 1,1-dioxide (Formula I: $R^1$=phenyl; $R^2$C(O)NH($CH_2$)$_2$-1-pyrrolidinyl; $R^3$=H; $R^4$=$CH(CH_3)_2$; $R^5$=6-$OCH_3$) as a white foam, m.p. 80°–84° C.

EXAMPLE 24

(a)

A mixture of 5 g (48 mmol) of malonic acid, 7.15 g (47.6 mmol) of 1-acetyl-2-phenylhydrazine, and 6.7 g of $PCl_3$ in 20 ml of THF was refluxed with stirring for 3 hours and cooled. After removing methanol in vacuo, ethanol was added and the resulting mixture was concentrated in vacuo. The resulting residue was triturated in methylene chloride to yield 2.2 g of a yellow solid. The solid was purified by column chromatography (silica gel; methylene chloride/methanol, 30/1–15/1) and crystallized from methylene chloride to afford 1.9 g (51%) of 2,4-dihydro-2-phenyl-5-hydroxy-3H-pyrazol-3-one (Formula III: $R^1$=Ph; $R^2$=OH; $R^3$=H) as a yellow solid.

(b)

A mixture of 2,4-dihydro-2-phenyl-5-hydroxy-3H-pyrazol-3-one (1 g, 5.7 mmol) and $POCl_3$ (1 g, 6.5 mmol) was heated at 100° C. for 4 hours and cooled. The mixture was diluted with ice/water and sodium bicarbonate solution was added (to pH=7). The aqueous layer was extracted with methylene chloride (3×), the organic layer was concentrated in vacuo, and the solid was crystallized from methylene chloride and recrystallized from acetonitrile and methylene chloride. The above solid was purified by column chromatography (silica gel, 6–33% ethyl acetate/hexane) to afford 110 mg of 2,4-dihydro-2-phenyl-5-chloro-3H-pyrazol-3-one (Formula III: $R^1$=Ph; $R^2$=Cl; $R^3$=H) and 56 mg of 1-phenyl-3-hydroxy-5-chloropyrazole as a white solid.

(c)

A mixture 2,4-dihydro-2-phenyl-5-chloro-3H-pyrazol-3-one (350 mg; 1.8 mmol), 2-bromomethyl-4-isopropyl-6-methoxy-1,2-benziso thiazol-3(2H)-one 1,1-dioxide (686 mg, 1.98 mmol), and KF (209 mg; 3.6 mmol) in DMF (8 ml) was stirred at 20° C. for 3 hours and the mixture was diluted with ice water. The above mixture was extracted with ether (3×) and the organic layer was dried over sodium sulfate, and concentrated in vacuo. The residue was purified by column chromatography (silica gel; 25–50% ethyl acetate/hexane; methylene chloride/hexane, 20–100%) and recrystallized from ethyl acetate/hexane to afford 265 mg (32%) of 4-isopropyl-6-methoxy-2-(1-phenyl-3-chloropyrazol-5-yl-oxymethyl)-1,2-benzisothiazol-3(2H)-one 1, 1-dioxide (Formula I: $R^1$=phenyl; $R^2$=Cl; $R^3$=H; $R^4$=CH(CH$_3$)$_2$; $R^5$=6-OCH$_3$) as a white solid, m.p. 109°–110° C.

EXAMPLE 25

To a mixture 2,4-dihydro-2-methyl-5-trifluoromethyl-3H-pyrazol-3-one (Formula III: $R^1$=CH$_3$; $R^2$=CF$_3$; $R^3$=H) (286 mg; 1.72 mmol) in 5 ml of DMF was added under nitrogen with stirring KF (166 mg, .2.86 mmol) and the mixture was stirred for 15 minutes. To the above mixture was added 2-bromomethyl-4-isopropyl-6-methoxy-1,2-benzisothiazol-3(2H)-one 1,1-dioxide (500 mg, 1.43 mmol) and the mixture was stirred at 20° C. for 1 hour. The mixture was diluted with cold saturated ammonium chloride solution. The above mixture was extracted with ether (3×) and the organic layer was dried over magnesium sulfate, and concentrated in vacuo. The residue was dissolved in methylene chloride and was purified by passing the solution through a plug of silica (30% ethyl acetate/hexane), followed by recrystallization from ether/hexane to afford 380 mg (61%) of 4-isopropyl-6-methoxy-2-(1-methyl-3-trifluoromethylpyrazol-5-yl-oxymethyl)-1,2-benzisothiazol-3(2H)-one 1,1-dioxide (Formula I: $R^1$=CF$_3$; $R^2$=CH$_3$; $R^3$=H; $R^4$=CH(CH$_3$)$_2$; $R^5$=6-OCH$_3$) as m.p. 107°–108° C.

EXAMPLE 26

(a)

A mixture of 2-chloropyrimidine (6 g, 52 mmol) and hydrazine hydrate (13.9 ml) in 100 ml of ethanol was stirred overnight under nitrogen. The mixture was cooled (0° C.) and the solid product was filtered, washed with cold ethanol, and dried in vacuo to afford 6 g (theory) of 2-hydrazinopyrimidine as a solid.

(b)

A mixture of 2 g (9 mmol) of 2-hydrazinopyrimidine and ethyl trifluoroacetoacetate (2.6 ml; 9.1 mmol) in 10 ml of acetic acid was refluxed for 60 hours with stirring under nitrogen and then cooled. The mixture was concentrated in vacuo, the residue was diluted with 100 ml of water, and the mixture was extracted with ethyl acetate (3×). The combined organic layer was dried over magnesium sulfate, and concentrated in vacuo. The resulting residue was dried in vacuo to afford 700 mg of 1-(2-pyrimidinyl)-3-trifluoromethyl-5-hydroxypyrazole as a red gum.

(c)

A mixture of 1-(2-pyrimidinyl)-3-trifluoromethyl-5-hydroxypyrazole (314 mg; 1.37 mmol) and KF (132 mg; 2.3 mmol) in 8 ml of DMF was stirred under nitrogen at room temperature and then 2-bromomethyl-4-isopropyl-6-methoxy-1,2-benzisothiazol-3(2H)-one 1,1-dioxide (400 mg, 1.14 mmol) was added. The reaction mixture was stirred at room temperature for 1.25 hours and diluted with cold saturated ammonium chloride solution. The mixture was extracted with ether (3×), the organic layer was dried over magnesium sulfate and then filtered and concentrated in vacuo. The yellow solid residue (495 mg) was dissolved in methylene chloride and was purified by column chromatography (silica gel; 20–40% ethyl acetate/hexane) and recrystallized from ether/hexane to afford 330 mg (60%) of 4-isopropyl-6-methoxy-2-[1-(2-pyrimidinyl)-3-(trifluoro methyl)pyrazol-5-yl-oxymethyl]-1,2-benzisothiazol-3(2H)-one 1,1-dioxide (Formula I: $R^1$=2-pyrimidinyl; $R^2$=CF$_3$; $R^3$=H; $R^4$=CH(CH$_3$)$_2$; $R^5$=6-OCH$_3$) as a white solid, m.p. 133°–134.5° C.

EXAMPLE 27

(a)

A mixture of 1.59 g (10 mmol) of 2-hydrazinoquinoline and ethyl trifluoroacetoacetate (1.5 ml, 10 mmol) in 5 ml of acetic acid was refluxed for 3 hours with stirring under nitrogen. The resulting solid mixture was partially concentrated in vacuo, and diluted with ether. The tan solid was filtered, the filtrate was washed with saturated sodium bicarbonate solution (3×), and the organic layer was concentrated in vacuo. The combined tan solid was crystallized from ether and dried to yield 1.325 g (47%) of 1 (2-quinolinyl)-3-trifluoromethyl-5-hydroxypyrazole, m.p. 145°–146° C.

(b)

A mixture of 1-(2-quinolinyl)-3-trifluoromethyl-5-hydroxypyrazole (533 mg; 1.91 mmol) and KF (220 mg; 3.8 mmol) in 35 ml of DMF was stirred under nitrogen at room temperature for 10 minutes and then 2-bromomethyl-4-isopropyl-6-methoxy-1,2-benzisothiazol-3(2H)-one 1,1-dioxide (592 mg, 1.7 mmol) was added. The reaction mixture was stirred at room temperature for 45 minutes and diluted with ice/cold saturated sodium bicarbonate solution. The mixture was extracted with ethyl acetate (3×) followed by the addition of ether, the organic layer was washed with water, dried over magnesium sulfate, and concentrated in vacuo. The residue was triturated with ethyl acetate/ether to yield a white solid, which was crystallized (from hot ethyl acetate/ether followed by methylene chloride/ether) and dried to afford 710 mg (76%) of 4-isopropyl-6-methoxy-2-[1-(2-quinolinyl)-3-(trifluoromethyl)pyrazol-5-yl-oxymethyl]-1,2-benzisothiazol-3(2H)-one 1,1-dioxide (Formula I: $R^1$=2-quinolinyl; $R^2$=CF$_3$; $R^3$=H; $R^4$=CH(CH$_3$)$_2$; $R^5$=6-OCH$_3$) as a white solid, m.p. 124°–125° C.

EXAMPLE 28

(a)

A mixture of 2,5-dichloropyridine (7.4 g, 50 mmol) and 50 ml of hydrazine hydrate (1 mol) was refluxed for 3 hours and the mixture was diluted with ether. The crystalline solid (1st crop) was filtered, the solid was washed with water; and the aqueous layer was extracted with ether (2×). The organic layer was partially concentrated in vacuo and filtered to yield an additional white solid (2nd crop). The concentration of the filtrate yielded more solid (third crop). The combined solid product was dried in vacuo to afford 5.95 g (82%) of 2-hydrazino-5-chloropyridine as a white solid, m.p. 116°–122° C.

(b)

A mixture of 1.445 g (10 mmol) of 2-hydrazino-5-chloropyridine and ethyl trifluoroacetoacetate (1.5 ml; 10 mmol) in 5 ml of acetic acid was refluxed overnight with stirring under nitrogen and then cooled. The mixture was concentrated in vacuo, the residue was diluted with ethyl acetate, and the solid mixture was filtered. The filtrate was washed with saturated sodium bicarbonate solution, the aqueous layer was extracted with ethyl acetate, and the combined organic layer was dried over magnesium sulfate. The organic layer was concentrated in vacuo, the residue was purified by flash chromatography (ethyl acetate) and crystallized (from ethyl acetate/hexane followed by hexane) to afford 1.42 g of 1-(5-chloro-2-pyridyl)-3-trifluoromethyl-5-hydroxy-pyrazole as a white solid, m.p. 58°–59° C.

(c)

A mixture of 1-(5-chloro-2-pyridyl)-3-trifluoromethyl-5-hydroxypyrazole (527 mg; 2 mmol) and KF (232 mg; 4 mmol) in 4 ml of DMF was stirred under nitrogen at room temperature for 20 minutes and then 2-bromomethyl-4-isopropyl-6-methoxy-1,2-benzisothiazol-3(2H)-one 1,1-dioxide (609 mg, 1.75 mmol) was added. The reaction mixture was stirred at room temperature for 1 hour, filtered, and the solid residue was washed with water. The white solid was dissolved in methylene chloride, dried over magnesium sulfate, partially concentrated in vacuo, and the resulting residue was crystallized from ethyl acetate. The combined solid was dried in vacuo to afford 736 mg (79%) of 4-isopropyl-6-methoxy-2-[1-(5-chloro-2-pyridyl)-3-(trifluoromethyl)pyrazol-5-yl-oxymethyl]-1,2-benzisothiazol-3(2H)-one 1,1-dioxide (Formula I: $R^1$=5-chloro-2-pyridyl; $R^2$=$CF_3$; $R^3$=H; $R^4$=$CH(CH_3)_2$; $R^5$=6-$OCH_3$) as a white solid, m.p. 173°–174° C.

EXAMPLE 29

(a)

To a solution of 2-furfuryl alcohol (8.24 g; 84 mmol) in 55 ml of acetic acid was added dropwise a solution of N,N,N',N'-tetraethyl-methylenediamine (20 g; 126 mmol)in 25 ml of acetic acid, and the solution was stirred at 0° C. for 30 minutes and at room temperature for 17 hours. The above solution was concentrated in vacuo, the residue was basified with dropwise addition of 30% of NaOH solution at 0° C. (to pH=11), and the mixture was extracted with ethyl acetate. The mixture was filtered, the organic layer was dried over sodium sulfate and concentrated in vacuo to yield a brown oil. The oil was distilled with a Kugelrohr Apparatus to afford 12.33 g (80%) of 5-diethylaminomethyl-2-hydroxymethylfuran as a yellow oil, b.p. 140° C./1 mm.

(b)

A solution of 5-diethylaminomethyl-2-hydroxymethylfuran (0.4 g; 2.18 mmol) in 5 ml of THF was added at 0° C. to a mixture of 4-isdpropyl-6-hydroxy-2-(1-phenyl-3-trifluoromethylpyrazol-5-yl- oxymethyl)-1,2-benzisothiazol-3(2H)-one 1,1-dioxide (1.0 g; 2.07 mmol) in 25 ml of THF containing $(Ph)_3P$ (550 mg; 2.09 mmol) and DEAD (380 mg; 2.18 mmol) and the resulting mixture was stirred at room temperature for 18 hours. The mixture was concentrated in vacuo and the residue was purified by flash chromatography (silica gel; methylene chloride, 80% ethyl acetate in methylene chloride), and fractional crystallization from hexane/ethyl acetate to afford 160 mg of 4-isopropyl-6-[1-(5-diethylaminomethyl-2-furfurylemethoxyl-2-(1-phenyl-3-trifluoromethylpyrazol-5-yl-oxymethyl)-1,2-benziso thiazol-3(2H)-one 1,1-dioxide (Formula I: $R^1$=Ph; $R^2$=$CF_3$; $R^3$=H; $R^4$=$CH(CH_3)_2$; $R^5$=6-[1-(5-diethylaminomethyl-2-furfuryl)methoxy]) as a solid, m.p. 108°–109° C.

EXAMPLE 30

(a)

A mixture of 5 g (27.2 mmol) of ethyl trifluoroacetoacetate and 4.86 g (27.2 mmol) of 2-chlorophenylhydrazine hydrochloride in 50 ml of acetic acid was heated at 100° C. with stirring overnight. The mixture was concentrated in vacuo (70° C.), the residue was disolved in methanol and concentrated in vacuo. The residue was triturated in methylene chloride, cooled (0° C.), and the white solid was filtered to afford 3.01 g (42%) of 2,4-dihydro-2-(2-chlorophenyl)-5-trifluoromethyl-3H-pyrazol-3-one (Formula III: $R^1$=2-Cl—Ph; $R^2$=$CF_3$; R3=H) as a white solid.

(b)

A mixture 2,4-dihydro-2-(2-chlorophenyl)-5-trifluoromethyl-3H-pyrazol-3-one (543 mg; 2.06 mmol), 2-bromomethyl-4-isopropyl-6-methoxy-1,2-benzisothiazol-3(2H)-one 1,1-dioxide (600 mg, 1.72 mmol) and KF (250 mg, 3.44 mmol) in 7 ml of DMF was stirred at room temperature for 4 hours. The mixture was diluted with water, extracted with ether (3×), and the organic layer was dried over sodium sulfate and concentrated in vacuo. The residue was purified by column chromatography (2×, silica gel; 12–50% ethyl acetate in hexane; 10–50% methylene chloride/ethyl acetate) and recrystallized from ethyl acetate/hexane to afford 392 mg (43%) of 4-isopropyl-6-methoxy-2-[1-(2-chlorophenyl)-3-trifluoromethylpyrazol-5-yl-oxymethyl]-1,2-benzisothiazol-3(2H)-one 1,1-dioxide (Formula I: $R^1$=2-Cl—Ph; $R^2$=$CF_3$; $R^3$=H; $R^4$=$CH(CH_3)_2$; $R^5$=6-$OCH_3$) as m.p. 134–1360° C.

EXAMPLE 31

(a)

A mixture of 2,4-dihydro-2-phenyl-5-ethoxycarbonyl-3H-pyrazol-3-one (5 g; 21.6 mmol) and 2-(diethylamino) ethyl-N-methylamine (3.09 g, 23.8 mmol) was heated at 140° C. under nitrogen overnight to yield an oily solid. The solid was purified by column chromatography (silica gel, methylene chloride/methanol, 6:1; TEA:methanol:methylene chloride 0.5:1:6). The above purified product was dissolved in water, extracted with methylene chloride, and the aqueous layer was concentrated in vacuo to yield an oily solid. The above solid was rechromatographed (silica gel, 6:1 methylene chloride/methanol; 6:1:1, methylene chloride/methanol/triethylamine) to afford 3.22 g (47%) of 2,4-dihydro-2-phenyl-5-[(O)N($CH_3$)($CH_2$)$_2$N(Et)$_2$]-3H-pyrazol-3-one (Formula III: $R^1$=Ph; $R^2$=[C(O)N($CH_3$)($CH_2$)$_2$N(Et)$_2$]; $R_3$=H) as an oily solid, m.p. 76°–80° C.

(b)

A mixture of 2-bromomethyl-4-isopropyl-6-methoxy-1,2-benzisothiazol-3(2H)-one 1,1-dioxide (696 mg, 2 mmol), 2,4-dihydro-2-phenyl-5-[C(O)N($CH_3$)($CH_2$)$_2$N(Et)$_2$]-3H-pyrazol-3-one (632 mg; 2 mmol), and KF (232 mg, 4 mmol) in 8 ml of DMF was stirred at room temperature for 1.5 hours, and the mixture was diluted with ice/water and filtered. The filtrate was basified with sodium bicarbonate (to pH=8) and extracted with ether (3×). The organic layer was dried over sodium sulfate, concentrated in vacuo, and the residue was purified by column chromatography (2×, silica gel, methylene chloride/methanol, 12:1) and recrystallized from ethyl acetete/hexane to afford 468 mg (40%) of 4-isopropyl-6-methoxy-2-[1-phenyl-3-]C(O) N(CH$_3$)(CH$_2$)$_2$N(Et)$_2$]-pyrazol-5-yl-oxymethyl]-1,2-benzisothiazol-3 (2H)-one 1,1-dioxide (Formula I: R$^1$=Ph; R$^2$=C(O)N(CH$_3$)(CH$_2$)$_2$N(Et)$_2$]; R$^3$=H; R$^4$=CH(CH$_3$)$_2$; R$^5$=6-OCH$_3$) as a white solid.

EXAMPLE 32

(a)

A mixture of 513 µl (3.46 mmol) of ethyl trifluoroacetoacetate and 0.5 g (3.46 mmol) of 3-chloro-6-hydrazinopyridazine in 2 ml of acetic acid was stirred at room temperature under nitrogen for 20 minutes and at 60° C. for 4 hours. The mixture was diluted with water and ethyl acetate, the aqueous layer was extracted with ethyl acetate (3×), and the combined organic layer was dried over magnesium sulfate and concentrated in vacuo to yield a solid (1.3 g). The solid was purified by flash chromatography on silica gel (20% ethyl acetate/hexane) and recrystallized from ethyl acetate/hexane to afford 450 mg of ethyl trifluoroacetoacetate 3-chloropyridazine-6-hydrazone as a white solid, m.p. 160°–161.5° C.

(b)

A mixture of 200 mg of ethyl trifluoroacetoacetate 3-chloropyridazine-6-hydrazone in 6 ml of toluene was refluxed under nitrogen for 5 hours. The mixture was concentrated in vacuo and the solid was recrystallized from ether/ethyl acetate to afford 180 mg of 1-(3-chloropyridazin-6-yl)-3-trifluoromethyl-5-hydroxy pyrazole as a pink solid.

(c)

To a mixture of 1-(3-chloropyridazin-6-yl)-3-trifluoromethyl-5-hydroxypyrazole (264 mg; 1 mmol) in DMF under nitrogen was added 96 mg (1.66 mmol) of KF and the mixture was stirred at 20° C. for 10 minutes. To the resulting mixture was added 2-bromomethyl-4-isopropyl-6-methoxy-1,2-benzisothiazol-3(2H)-one 1,1-dioxide (289 mg, 0.83 mmol) and the resulting mixture was stirred at room temperature (20° C.) for 1 hour and poured into saturated ammonium chloride solution/ethyl acetate. The aqueous layer was extracted with ethyl acetate (3×), the combined organic layer was dried over magnesium sulfate and concentrated in vacuo. The residue was purified by flash chromatography (silica gel; 20% ethyl acetate in hexane) and recrystallized from ether/hexane to afford 337 mg (77%) of 4-isopropyl-6-methoxy-2-[1-(3-chloropyridazin-6-yl)-3-trifluoromethylpyrazol-5-yl-oxymethyl]-1,2-benzisothiazol-3(2H)-one 1,1-dioxide (Formula I: R$^1$=3-Cl-6-pyridazinyl; R$^2$=CF$_3$; R$^3$=H; R$^4$=CH(CH$_3$)$_2$; R$^5$=6-OCH$_3$) as a white solid, m.p. 110°–1110° C.

EXAMPLE 33

(a)

To condensed isobutylene (1 ml) in a resealable glass tube was added 1-phenyl-3-carboxy-5-hydroxypyrazole (1 g; 4.9 mmol) in 30 ml of dioxane. The reaction mixture was cooled to −78° C. and 0.5 ml of conc. sulfuric acid was then added. The tube was sealed, stirred at room temperature for 6 hours,
and cooled. The tube was opened, the mixture was neutralized and then basified (pH=12) with 2N NaOH solution, and extracted with ethyl acetate (3×). The combined organic layer was dried over magnesium sulfate and concentrated in vacuo to afford 431 mg of 1-phenyl-3-(t-butyloxycarbonyl)-5-hydroxypyrazole as a white solid.

(b)

To a mixture of 1-phenyl-3-(t-butyloxycarbonyl)-5-hydroxypyrazole in 12 ml of DMF was added under nitrogen at room temperature KF (155 mg, 2.86 mmol) and the mixture was stirred for 10 minutes. To the above mixture was added 2-bromomethyl-4-isopropyl-6-methoxy-1,2-benzisothiazol-3 (2H)-one 1,1-dioxide (500 mg, 1.43 mmol), the mixture was stirred at room temperature for 2.3 hours, and the mixture was diluted with water/ether. The mixture was extracted with ether (3×) and the combined organic layers were dried over magnesium sulfate, concentrated in vacuo, and the residue was purified by flash chromatography (silica gel, 20% ethyl acetate/hexane) and recrystallized from ether/hexane to afford 200 mg of 4-isoorooyl-6-methoxy-2-[1-phenyl-3-(t-butoxycarbonyl)pyrazol-5-yl-oxymethyl]-1,2-benzisothiazol-23 (2H)-one 1,1-dioxide (Formula I: R$^1$=Ph; R$^2$=C(O)To—Bu; R$^3$=H; R$^4$=CH(CH$_3$)$_2$; R$^5$=6-OCH$_3$) as a white solid, m.p. 203°–204° C.

EXAMPLE 34

(a)

A mixture of 1.38 ml (9.4 mmol) of ethyl trifluoroacetoacetate and 2.0 g (9.4 mmol) of 5-chloro-3-trifluoromethylpyridyl-2-hydrazine in 7 ml of acetic acid was heated at 60° C. for 1 hour and refluxed for 3 hours under nitrogen with stirring. The mixture was cooled, diluted with water/ethyl acetate, the aqueous layer was neutralized (to pH=7) with saturated sodium bicarbonate solution and extracted with ethyl acetate (3×). The combined organic layer was dried over magnesium sulfate and concentrated in vacuo. The residue (an amber oil) was purified by flash chromatography (silica gel, 20%–75% ethyl acetate/hexane to afford 2.4 g of ethyl trifluoroacetoacetate 5-chloro-3-trifluoromethylpyridyl-2-hydrazone as a yellow oil and 440 mg of 1-(5-chloro-3-trifluoromethyl-2-pyridyl)-3-trifluoromethyl-5-hydroxypyrazole as a tan solid.

(b)

To a mixture 1-(5-chloro-3-trifluoromethyl-2-pyridyl)-3-trifluoromethyl-5-hydroxypyrazole (440 mg; 1.30 mmol) in 8 ml of DMF was added under nitrogen KF (132 mg, 2.28 mmol) and the mixture was stirred at room temperature for 10 minutes. To the above mixture was added 2-bromomethyl-4-isopropyl-6-methoxy-1,2-benzisothiazol-3(2H)-one 1,1-dioxide (400 mg, 1.14 mmol) and the resulting mixture was stirred at room temperature for one hour. The mixture was quenched with cold saturated ammonium chloride solution, diluted with water, and extracted with ether (3×). The combined organic layer was dried over magnesium sulfate and concentrated in vacuo. The residue (an oil) was purified by flash chromatography (silica gel; 20% ethyl acetate in hexane) and recrystallized from ether/hexane to afford 343 mg (50%) of 4-isopropyyl-6-methoxy-2-[1-(5-chloro-3-trifluoromethyl-2-pyridyl)-3-trifluoromethylpyrazol-5-yl-oxymethyl]-1,2-benzisothiazol-3(2H)-one 1,1-dioxide (Formula I: R$^1$=3-CF$_3$-5-Cl-2-pyridyl; R$^2$=CF$_3$; R$^3$=H; R$^4$=CH(CH$_3$)$_2$; R$^5$=6-OCH$_3$) as a white solid, m.p. 141°–142° C.

27

EXAMPLE 35

A mixture of 2,4-dihydro-2-phenyl-5-cyano-3H-pyrazol-3-one (Formula III: $R^1$=Ph; $R^2$=CN; $R^3$=H) (366 mg; 1.98 mmol), 2-bromomethyl-4-isopropyl-6-methoxy-1,2-benzisothiazol-3(2H)-one 1,1-dioxide (689 mg, 1.98 mmol), and KF (230 mg, 3.91 mmol) in 8 ml of DMF was stirred at room temperature for 3 hours and the resulting mixture was diluted with ice/water. The solid product was filtered, the residual solid was redissolved in ether/water, and the aqueous layer was extracted with ether (3×). The combined organic layer was dried over magnesium sulfate and concentrated in vacuo, and the residue was purified by column chromatography (silica gel; 12–50% ethyl acetate in hexane) and recrystallized from ethyl acetate/hexane to afford 420 mg (47%) of 4-isopropyl-6-methoxy-2-(1-phenyl-3-cyanopyrazol-5-yl-oxymethyl)-1,2-benziso thiazol-3(2H)-one 1,1-dioxide (Formula I: $R^1$=Ph; $R^2$=CN; $R^3$=H; $R^4$=CH($CH_3$)$_2$; $R^5$=6-$OCH_3$) as a white solid, m.p. 114°–116° C.

EXAMPLE 36

(a)

A mixture of 0.8 ml (5.6 mmol) of ethyl trifluoroacetoacetate and 1.0 g (5.6 mmol) of 6-trifluoromethylpyridyl-2-hydrazine in 5 ml of acetic acid was heated at 60° C. for 2 hours and refluxed for 5 hours under nitrogen with stirring. The mixture was cooled, diluted with water/ethyl acetate, and the aqueous layer was neutralized (to pH=7) with saturated sodium bicarbonate solution and extracted with ethyl acetate (3×). The combined organic layer was dried over magnesium sulfate and concentrated in vacuo. The residue (an oil, 1.7 g) was purified by flash chromatography (silica gel, ethyl acetate/hexane) to afford 1 g of ethyl trifluoroacetoacetate 6-trifluoromethylpyridyl-2-hydrazone as an oil and 420 mg of 1-(6-trifluoromethyl-2-pyridyl)-3-trifluoromethyl-5-hydroxypyrazole as a solid.

(b)

To a mixture 1-(6-trifluoromethyl-2-pyridyl)-3-trifluoromethyl-5-hydroxypyrazole (420 mg; 1.41 mmol) in 10 ml of DMF was added under nitrogen KF (132 mg, 2.28 mmol) and the mixture was stirred at room temperature for 10 minutes. To the above mixture was added 2-bromomethyl-4-isopropyl-6-methoxy-1,2-benzisothiazol-3(2H)-one 1,1-dioxide (410 mg, 1.17 mmol) and the resulting mixture was stirred at room temperature for one hour, quenched with cold saturated ammonium chloride solution, and extracted with ether (3×). The combined organic layer was dried over magnesium sulfate and concentrated in vacuo. The residue (a solid) was purified by flash chromatography (silica gel; 5–20% ethyl acetate in hexane) and recrystallized from ether/hexane to afford 420 mg (63%) of 4-isopropyl-6-methoxy-2-[1-(6-trifluoromethyl-2-pyridyl)-3-trifluoromethylpyrazol-5-yl-oxymethyl]-1,2-benzisothiazol-3(2H)-one 1,1-dioxide (Formula I: $R^1$=6-$CF_3$-2-pyridyl; $R^2$=$CF_3$; $R^3$=H; $R^4$=CH($CH_3$)$_2$; $R^5$=6-$OCH_3$) as a white solid, m.p. 149°–150° C.

EXAMPLE 37

(a)

A mixture of 2-bromomethyl-4-isopropyl-6-methoxy-1,-2-benzisothiazol-3(2H)-one 1,1-dioxide (44 g, 126.4 mmol) and $BBr_3$ (1.0M in methylene chloride, 164.4 mmol) was allowed to reflux for 48 hours and then poured into ice/water. The mixture was filtered, the aqueous layer was extracted with ethyl acetate, and the mixture of the combined organic layer and the residue (from above filtration) was dried over sodium sulfate and concentrated in vacuo. The solid residue was recrystallized from toluene/cyclohexane (7:2) to afford 52.6 g (96 %) of 2-bromomethyl- 4-isopropyl-6-hydroxy-1,2-benzisothiazol-3 (2H)-one 1,1-dioxide as solid, m.p. 167°–169° C.

(b)

A mixture of 44 ml (0.3 mol) of ethyl trifluoroacetoacetate and 33 mL (335.4 mmol) of phenylhydrazine in 60 ml of methanol containing 6 ml of conc. HCl solution was refluxed with stirring for 1.5 hours. After adding activated charcoal with stirring, the hot mixture was filtered. The residue was washed with methanol (2×70 ml), diluted with water, and the resulting white solid was filtered. The solid was washed with hexane and dried to afford 54.3 g (79%) of 1-phenyl-3-trifluoromethyl-5-hydroxypyrazole as a pale solid.

(c)

A mixture 1-phenyl-3-trifluoromethyl-5-hydroxypyrazole (20.5 g; 89.92 mmol) and $Cs_2CO_3$ (17.6 g; 53.8 mmol) in methanol (50 ml) was stirred at 20° C. for 5 hours. The solvent was concentrated in vacuo, and the residue was dried in vacuo at 50° C. for 4 hours. To a solution of the above residue in 50 ml of DMF was added 2-bromomethyl-4-isopropyl-6-hydroxy-1,2-benzisothiazol-3(2H)-one 1,1-dioxide (25 g, 74.9 mmol) and the resulting mixture was stirred at room temperature (20° C.) overnight and poured into ether/brine. The above mixture was extracted with ether and the combined organic layer was dried over sodium sulfate, and concentrated in vacuo. The residue (46 g) was purified by column chromatography (silica gel; chloroform, 2% ethyl acetate in chloroform) and recrystallized from hexane to afford 25.7 g (71%) of 4-isopropyl-6-hydroxy-2-(1-phenyl-3-trifluoromethylpyrazol-5-yl-oxymethyl)-1,2-benzisothiazol-3(2H)-one 1,1-dioxide (Formula I: $R^1$=Ph; $R^2$=$CF_3$; $R^3$=H; $R^4$=CH($CH_3$)$_2$; $R^5$=6-OH) as a white solid.

(d)

A mixture of 6-hexanolactone (40 g, 0.35 mol), phenylmethanol (70 g, 0.647 mol), and conc. sulfuric acid (40 drops) was heated at 50° C. overnight. The resulting mixture was purified by column chromatography (hexane, 5–30% ethyl acetate/hexane) and distilled to afford 20.1 g (26%) of 6-hydroxyhexanoic acid phenylmethyl ester, b.p. 70°–75° C./1 mm.

(e)

A mixture of 4-isopropyl-6-hydroxy-2-(1-phenyl-3-trifluoromethylpyrazol-5-yl-oxymethyl)-1,2-benzisothiazol-3(2H)-one 1,1-dioxide (6 g; 12.46 mmol), 6-hydroxyhexanoic acid phenylmethyl ester (4.2 g;14.96 mmol), DEAD (4.35 g; 24.9 mmol) and(Ph)$_3$P (6.54 g; 24.93 mmol) in methylene chloride (100 ml) was combined with cooling in ice/water and then was stirred at room temperature overnight. The mixture was concentrated in vacuo and the residue was purified by flash chromatography (silica gel; 20–80% ethyl acetate/hexane) to afford 2.5 g (29%) of 4-isopropyl-6-[5-(phenylmethyloxycarbonyl)pentyloxy]-2-(1-phenyl-3-trifluoromethyl pyrazol-5-yl-oxymethyl)-1,2-benzisothiazol-3(2H)-one 1,1-dioxide (Formula I: $R^1$=Ph; $R^2$=$CF_3$; $R^3$=H; $R^4$=CH($CH_3$)$_2$; $R^5$=6-O($CH_2$)$_5$C(O)$OCH_2H$) as a solid.

(f)

A mixture of 4-isopropyl-6-[5-(phenylmethyloxycarbonyl)- pentyloxy]-2-(1-phenyl-3-trifluoromethylpyrazol-5-yl-oxymethyl)- 1,2-benzisothiazol-3(2H)-one 1,1-dioxide (3.675 g; 5.258 mmol) and 1.5 g of 10% Pd/C in ethyl acetate was hydrogenated (hydrogen balloon). The catalyst was removed on a pad of CELITE® and the filtrate was concentrated in vacuo to afford 2.97 g (93%) of 4-isopropyl-6-[5-(carboxy)-enthyloxy]-2-(1-phenyl-3-trifluoromethyl pyrazol-5-yl-oxymethyl)-1,2-benzisothiazol-3(2H)-one 1,1-dioxide (Formula I: $R^1$=Ph; $R^2$=$CH_3$; $R^3$=H; $R^4$=$CH(CH_3)_2$; $R^5$=6-$O(CH_2)_5CO_2H$) as a solid, m.p. 140°–142° C.

EXAMPLE 38

(a)

A mixture of butyrolactone (21.5 g, 250 mmol) and methyl iodide (100 g, 704 mmol) was added with stirring to a refluxing suspension of NaH (25 g, 629 mmol) in 250 ml of dioxane over a period of 40 minutes, and the resulting mixture was refluxed for 2 hours and poured into ice/water. The mixture was acidified with 10% HCl solution and extracted with ether (4×). The organic layer was washed with brine, dried over sodium sulfate, and concentrated in vacuo to yield a residue (white and red layers). The red layer was distilled to afford 8.17 g of 2,2-dimethylbutyrolactone as a red oil, b.p. 105–118° C./80 mm.

(b)

A mixture of 2,2-dimethylbutyrolactone (8.17 g, 71.7 mmol) and KOH (4.02 g,71.7 mmol) in 72 ml of water was refluxed overnight and then the mixture was concentrated in vacuo (50° C.). The crude residual oil was crystallized in ethanol/ether and the resulting white solid product was filtered and dried (100° C./0.1 mm) to afford 10.6 g (87%) of 4-hydroxy-2,2-dimethylbutyric acid monopotassium salt.

A mixture of 4-hydroxy-2,2-dimethylbutyric acid monopotassium salt (10.6 g,62.35 mmol) and phenylmethyl bromide (11.63 g, 68 mmol) in 100 ml of DMF was stirred at room temperature for 24 hours and then the mixture was poured into ice/water. The mixture was extracted with ether (3×) and the organic layer was washed with brine, dried over sodium sulfate, and concentrated in vacuo. The residue was purified by column chromatography (silica, 12–66% of ethyl acetate/hexane) to afford 10.02 g (72%) of 4-hydroxy-2,2-dimethylbutyric acid phenylmethyl ester.

(c)

A mixture of 4-isopropyl-6-hydroxy-2-(1-phenyl-3-trifluoromethylpyrazol-5-yl-oxymethyl)-1,2-benzisothiazol-3(2H)-one 1,1-dioxide (7 g; 14.55 mmol), 4-hydroxy-2,2-dimethylbutyric acid phenylmethyl ester (3.88 g;17.46 mmol), DEAD (3.04 g; 17.46 mmol) was dissolved in 180 ml of THF at 00C and then $(Ph)_3P$ (4.575 g; 17.46 mmol) was added at 0° C. The above mixture was stirred overnight at room temperature and concentrated in vacuo, and the residue was purified by column chromatography (2×, silica gel; 12–33% ethyl acetate/ hexane;methylene chloride/hexane, 1/4-30/1) to afford 3.65 g (37%) of 4-isopropyl-6-[3-methyl-3-(phenylmethyloxycarbonyl)butoxy]-2-(1-phenyl-3-trifluoromethylpyrazol-5-yl-oxymethyl)-1,2-benzisothiazol-3 (2H)-one 1,1-dioxide (Formula I: $R^1$=Ph; $R^2$=$CF_3$; $R^3$=H; $R^4$=$CH(CH_3)_2$; $R^5$=6-$O(CH_2)_2C(CH_3)_2CO_2Ph$) as a solid.

(d)

A mixture of 4-isopropyl-6-[3-methyl-3-(phenylmethyloxycarbonyl)butoxy]-2-(1-phenyl-3-trifluoromethylpyrazol-5-yl-oxymethyl)-1,2-benzisothiazol-3(2H)-one 1,1-dioxide (3.52 g; 5.14 mmol) and 0.8 g of 10% Pd/C in ethyl acetate (80 ml) was placed in the Parr Apparatus and hydrogenated at 50 psi for 2 hours. The catalyst was removed on a pad of CELITE®, the filtrate was concentrated in vacuo, and the residue was purified by column chromatography (2×, silica gel; methylene chloride/ methanol, 20/1) to afford 2.75 g (90%) of 4-isopropyl-6-[3-methyl-3-(carboxy)butoxy-2-(1-phenyl-3-trifluoromethylpyrazol-5-yl-oxymethyl)-1,2-benzisothiazol-3(2H)-one 1,1-dioxide (Formula I: $R^1$=Ph; $R^2$=$CF_3$; $R^3$=H; $R^4$=$CH(CH_3)_2$; $R^5$=6-$O(CH_2)_2C(CH_3)_2CO_2H$) as a solid, m.p. 141°–144° C.

EXAMPLE 39

(a)

A mixture of 1-(4-chlorophenyl)-3-trifluoromethyl-5-hydroxypyrazole (8.4 g; 32 mmol) and $Cs_2CO_3$ (5.22 g; 16 mmol) in methanol (140 ml) was stirred at room temperature for 1.5 hours. The solvent was concentrated in vacuo, and the residue was dried in vacuo overnight. To the above residue was added 133 ml of DMF, cooled to 0° C., and 2-bromomethyl-4-isopropyl-6-hydroxy-1,2-benzisothiazol-3(2H)-one 1,1-dioxide (5.33 g, 16 mmol) and the resulting mixture was stirred at room temperature for 24 hours and poured into ice/water. The resulting solid was filtered, the solid was dissolved in ether (700 ml), the organic layer was washed with brine (2×200 ml), and concentrated in vacuo. The residue was purified by column chromatography (silica gel; 14–75% ethyl acetate/hexane) and recrystallized from methanol to afford 4.54 g (55%) of 4-isopropyl-6-hydroxy-2-[1-(4-chlorophenyl)-3-trifluoromethylpyrazol-5-yl-oxymethyl]-1,2-benzisothiazol-3(2H)-one 1,1-dioxide (Formula I: $R^1$=4-Cl—Ph; $R^2$=$CH_3$; $R^3$=H; $R^4$=$CH(CH_3)_2$; $R^5$=6-OH) as a white solid.

(b)

A mixture of 4-isopropyl-6-hydroxy-2-[1-(4-chlorophenyl)-3-trifluoromethylpyrazol-5-yl-oxymethyl]-1, 2-benzisothiazol-3(2H)-one 1,1-dioxide (9.95 g; 19.3 mmol), 4-hydroxybutanoic acid phenylmethyl ester (4.49 g;23.16 mmol), DEAD (4.03 g; 23.16 mmol) was dissolved in 193 ml of THF at 0° C. and then $(Ph)_3P$ (6.068 g; 23.16 mmol) was added at 0° C. The above mixture was stirred overnight at room temperature, concentrated in vacuo, and the residue was purified by column chromatography (2×, silica gel; 12–50% ethyl acetate/hexane; methylene chloride/hexane, 1/4-30/1) to afford 4.55 g (34%) of 4-isopropyl-6-[3-(phenylmethyloxycarbonyl)propoxy]-2-[1-(4-chlorophenyl)-3-trifluoromethylpyrazol-5-yl-oxymethyl]-1,2-benzisothiazol-3(2H)-one 1,1-dioxide (Formula I: $R^1$=4-Cl—Ph; $R^2$=$CF_3$; $R^3$=H; $R^4$=$CH(CH_3)_2$; $R^5$=6-$O(CH_2)_3CO_2CH_2Ph$) as a solid.

(c)

A mixture of 4-isopropyl-6-[3-(phenylmethyloxycarbonyl)propoxy]-2-[1-(4-chlorophenyl)-3-trifluoromethylpyrazol-5-yl-oxymethyl]-1,2-benzisothiazol-3(2H)-one 1,1-dioxide (4.19 g; 6.055 mmol) and 50 ml of 20% sulfuric acid in 80 ml of dioxane was heated at 100° C. for 20 hours. The mixture was cooled, poured into ice, neutralized with sodium bicarbonate solution (160 ml, to pH=5), and the resulting solid was filtered and recrystallized (3×, ethyl acetate/hexane; methylene chloride/hexane; and acetonitrile) to afford 2.56 g of 4-isopropyl-6-[3-(carboxy)propoxy]-2-[1-(4-chlorophenyl)-3-trifluoromethylpyrazol-5-yl-oxymethyl]-1,2-benzisothiazol-3(2H)-one 1,1-dioxide (Formula I: $R^1$=4-Cl—Ph; $R^2$=$CF_3$; $R^3$=H; $R^4$=$CH(CH_3)_2$; $R^5$=6-$O(CH_2)_3CO_2H$) as a white solid, 162°–164° C.

EXAMPLE 40

(a)

A mixture of 4-butyrolactone (4 ml, 0.052 mol) and N-methyl-N',N'-diethylethylenediamine (8.2 ml, 0.052 mol) under nitrogen was heated at 140° C. for 6 hours and then cooled. The mixture was distilled with Kugelrohr apparatus to afford 7.5 g of 4-hydroxybutanoic acid N,N-diethylaminoethyl-N'-methylamide as an oil, which was further purified by flash chromatography (2×; acetone; acetone/hexane) to afford 5.5 g of the product.

(b)

To a solution of 4-isopropyl-6-hydroxy-2-(1-phenyl-3-trifluoromethylpyrazol-5-yl-oxymethyl)-1,2-benzisothiazol-3(2H)-one 1,1-dioxide (4.32 g; 9 mmol) in 100 ml of methylene chloride was added dropwise at 0- –5° C. $(Ph)_3P$ (3.64 g; 13.9 mmol) and then diethylazodicarboxylate (DEAD) (2.42 g; 13.9 mmol) and in methylene chloride (20 ml) over a period of 15 minutes. To the above mixture was added 4-hydroxybutanoic acid N,N-diethylaminoethyl-N'-methylamide (2.72 g; 12.6 mmol) in 20 ml of methylene chloride over a period of 15 minutes. The above mixture was stirred at room temperature overnight, concentrated in vacuo, and the residue was purified by flash chromatography (3×; 40–70% acetone/hexane; acetone, 10% methanol/toluene) to afford 3.51 g of 4-isopropyl-6-[$O(CH_2)_3C(O)N(CH_3)(CH_2)_2N(Et)_2$]-2-(1phenyl-3-trifluoromethyl pyrazol-5-yl-oxymethyl)-1,2-benzisothiazol-3(2H)-one 1,1-dioxide (Formula I: $R^1$=Ph; $R^2$=$CF_3$; $R^3$=H; $R^4$=CH $(CH_3)_2$; $R^5$=6-$O(CH_2)_3C(O)N(CH_3)(CH_2)_2N(Et)_2$) as a foam.

EXAMPLE 41

A solution of 4-isopropyl-6-[5-(carboxy)pentyloxy]-2-(1-phenyl-3-trifluoromethylpyrazol-5-yl-oxymethyl)-1,2-benzisothiazol-3(2H)-one 1,1-dioxide (2.3 g, 3.86 mmol) in $CH_2Cl_2$ (25 mL) at 0° C. was stirred for 15 minutes then triethylamine (0.57 mL, 4.053 mmol), followed by isobutyl chloroformate (0.53 mL, 4.053 mmol) were added. The reaction mixture was stirred for 20 minutes, then N,N,N'-triethylethylenediamine (0.7 mL, 4.285 mmol) was added and the reaction mixture was warmed to room temperature and stirred for 2 hours. The reaction mixture was loaded onto a silica gel column and eluted with AcOH/MeOH/$CH_2Cl_2$ (1/4/95) followed by 10% MeOH/$CH_2Cl_2$ and the product fractions were dissolved in $CH_2Cl_2$, washed with aqueous sodium bicarbonate, dried over $Na_2SO_4$, filtered and concentrated to afford 2.3 g (82%) of 4-isopropyl-6-[5-[$Et_2N(CH_2)_2N(Et)C(O)$]pentyloxy]-2-(11-phenyl-3-trifluoromethyl pyrazol-5-yl-oxymethyl)-1,2-benzisothiazol-3(2H)-one 1,1-dioxide (Formula I: $R^1$=Ph; $R^2$=$CH_3$; $R^3$=H; $R^4$=$CH(CH_3)_2$; $R^5$=6-$O(CH_2)_5C(O)N(Et)(CH_2)_2N(Et)_2$) as a clear viscous liquid.

EXAMPLE 42

(a)

A mixture of the sodium salt of 2-carboxy-5-hydroxyfuran (3.33 g, 20.28 mmol), 4-methoxybenzyl chloride (3.29 g, 21.0 mmol) and DMF (20 mL) was heated at 70° C. for 5.5 hours. The reaction mixture was poured into ice-water, extracted with ethyl acetate and concentrated to afford 6.3 g of crude product. The crude product was combined with 2.7 g of crude product from a similar experimental run and the mixture was purified by column chromatography on silica gel eluting with 2.5% EtOAc/$CH_2Cl_2$ to 50% EtOAc/$CH_2Cl_2$ to afford 5.63 g of 2-(4-methoxyphenylmethyl oxycarbonyl)-5-hydroxymethylfuran.

(b)

To a solution of 4-isopropyl-6-hydroxy-2-(1-phenyl-3-trifluoromethylpyrazol-5-yl-oxymethyl)-1,2-benzisothiazol-3(2H)-one 1,1-dioxide (5.29 g, 10.986 mmol) in THF (60 mL) was added $PPh_3$ (3.46 g, 13.183 mmol), diethylazodicarboxylate (2.3 g, 13.183 mmol) and 2-(4-methoxyphenylmethyloxycarbonyl)-5-hydroxymethylfuran (3.46 g, 13.183 mmol). Upon completion of the reaction, the mixture was stripped, the residue was dissolved in $CH_2Cl_2$ (100 mL) and silica gel (20 g) was added. The solvent was stripped and the residue was purified by flash chromatography eluting with 20% ethyl acetate/hexane to 30% ethyl acetate/hexane to afford 4.97 g (62%) of 4-isopropyl-6-[1-(5-(4-methoxyphenylmethyloxycarbonyl-2-furanyl) methoxy]-2-[1-phenyl-3-trifluoromethylpyrazol-5-yl-oxymethyl]-1,2-benzisothiazol-3(2H)-one 1,1-dioxide (Formula I: $R^1$=Ph; $R^2$=$CF_3$; $R^3$=H; $R^4$=$CH(CH_3)_2$; $R^5$=6-[1-(5-(C(O)$OCH_2Ph$-4-$OCH_3$)-2-furanyl) methoxy]), m.p. 68°–75° C.

(c)

A mixture of 4-isopropyl-6-[1-(5-(4-methoxyphenylmethyloxy carbonyl-2-furanyl) methoxy]-2-[1-phenyl-3-trifluoromethylpyrazol-5-yl-oxymethyl]-1,2-benzisothiazol-3(2H)-one 1,1-dioxide (5.75 g, 5.17 mmol), trifluoroacetic acid (8 mL) and anisole (50 mL) was heated at 50° C. for 4 hours. The reaction mixture was cooled, hexane (150 mL) was added and the precipitate which formed was collected by filtration to afford 2.74 g of 4-isopropyl-6-[1-(5-(carboxy-2-furanyl)methoxy]-2-[1-phenyl-3-trifluoromethylovrazol-5-yl-oxymethyl]- 1,2-benzisothiazol-3(2H)-one 1,1-dioxide (Formula I: $R^1$=Ph; $R^2$=$CF_3$; $R^3$=H; $R^4$=$CH(CH_3)_2$; $R^5$=6-[1-(5-carboxy-2-furanyl) methoxy]), m.p. 212°–213° C.

EXAMPLE 43

To a solution of 4-isopropyl-6-[1-(5-(carboxy-2-furanyl) methoxy]-2-[1-phenyl-3-trifluoromethylpyrazol-5-yl-oxymethyl]-1,2-benzisothiazol-3(2H)-one 1,1-dioxide (1.53 g, 2.53 mmol) in $CH_2Cl_2$ at 0° C. was added triethylamine (0.39 mL, 2.78 mmol) and isobutyl chloroformate (0.36 mL, 2.78 mmol) followed 20 minutes later by N,N,N'-triethylethylenediamine (0.45 mL, 2.8 mmol). The reaction mixture was stirred for about 3 hours, extra triethylamine (4 mL) and N,N,N'-triethylethylenediamine (0.2 mL) were added and the mixture was stirred for one hour. The reaction mixture was loaded onto silica gel (5 g), the solvent was removed and the residue was flashed through a silica gel column eluting with 100% acetone, then methanol(4%)/AcOH(1%)/$CH_2Cl_2$(95%) to afford 1.85 g (92%) of 4-isopropyl-6-[1-(5-[$Et_2N(CH_2)_2N(Et)C(O)$-2-furanyl) methoxy]-2-[1-phenyl-3-trifluoromethylpyrazol-5-yl-oxymethyl]-1,2-benzisothiazol-3(2H)-one 1,1-dioxide (Formula I: $R^1$=Ph; $R^2$=$CF_3$; $R^3$=H; $R^4$=$CH(CH_3)2$; $R^5$=6-[1-(5-(C(O)N(Et)($CH_2)_2NEt_2$)-2-furanyl)methoxy]).

EXAMPLE 44

To a solution of 4-isopropyl-6-[3-(carboxy)propoxy]-2-[1-(4-chlorophenyl)-3-trifluoromethylpyrazol-5-yl-oxymethyl]-1,2-benzisothiazol-3(2H)-one 1,1-dioxide (200 mg, 0.289 mmol) in $CH_2Cl_2$ at 0° C. was added triethylamine (32 mg, 0.318 mmol), followed by isobutyl chloroformate (43.4 mg, 0.318 mmol). The reaction mixture was stirred at 0° C. for 30 minutes and then N,N-diethyl-N'-methylethylenediamine (45 mg, 0.347 mmol) was added. The mixture was stirred at 0° C. for 30 minutes, then at 20° C. for 2.5 hours. The mixture was concentrated and the residue was purified by column chromatography on silica gel eluting with $CH_2Cl_2/CH_3OH/HOAc$ to afford 138 mg (61%) of 4-isopropyl-6-[O(CH$_2$)$_3$C(O)N(CH$_3$) (CH$_2$)$_2$N(Et)$_2$]-2-[1-(4-chlorophenyl)-3-trifluoromethylpyrazol-5-yl-oxymethyl]-1,2-benzisothiazol-3(2H)-one 1,1-dioxide (Formula I: $R^1$=4-Cl—Ph; $R^2$=CF$_3$ ; $R^3$ =H; $R^4$=CH (CH$_3$)$_2$; $R^5$=6-O(CH$_2$)$_3$C(O)N(CH$_3$)(CH$_2$)$_2$N(Et)$_2$), as an off-white solid.

EXAMPLE 45

(a)

A mixture of 3-methyl-2-pyridylhydrazine (1.0 g, 8.13 mmol), acetic acid (7.0 mL) and ethyl trifluoroacetoacetate (1.2 mL, 8.13 mmol) was heated at 60° C. for 9 hours. The reaction mixture was neutralized with $NaHCO_3$ and then was extracted with EtOAc (3×). The EtOAc extracts were combined, dried over $MgSO_4$, filtered and concentrated to afford crude product which was purified by column chromatography on silica gel to afford 200 mg of 1-(3-methyl-2-pyridyl)-3-trifluoromethyl-5-hydroxypyrazole.

(b)

To a solution of 1-(3-methyl-2-pyridyl)-3-trifluoromethyl-5-hydroxypyrazole (200 mg, 0.823 mmol) in DMF (1 mL) was added KF (87 mg, 1.494 mmol), followed 10 minutes later by 2-bromomethyl-4-isopropyl-6-methoxy-1,2-benzisothiazol-3(2H)-one 1,1-dioxide (260 mg, 0.748 mmol). The mixture was stirred for 2 hours and then was quenched with saturated $NH_4Cl$ and extracted with ether (3×). The ether extracts were combined, dried over $MgSO_4$, filtered and concentrated to afford 390 mg of crude product. The crude product was purified by column chromatography on silica gel eluting with 2% acetone/$CH_2Cl_2$ to 10% acetone/$CH_2Cl_2$ to afford, after recrystallization from ether, 180 mg (47%) of 4-isopropyl-6-methoxy-2-[1-(3-methyl-2-pyridyl)-3-trifluoromethylpyrazol-5-yl-oxymethyl]-1,2-benzisothiazol-3(2H)-one 1,1-dioxide (Formula I: $R^1$=3-methyl-2-pyridyl; $R^2$=CF$_3$; $R^3$=H; $R^4$=CH (CH$_3$)$_2$; $R^5$=6-OCH$_3$) as a white solid, m.p. 143°–144° C.

EXAMPLE 46

A mixture of 1-(4-chlorophenyl)-3-cyano-5-hydroxypyrazole (59.7 mg, 0.273 mmol), 2-bromomethyl-4-isopropyl-6-methoxy-1,2-benzisothiazol-3(2H)-one 1,1-dioxide (93.7 mg, 0.27 mmol), KF (15.7 mg, 0.27 mmol) and DMF (5 mL) was stirred at room temperature for 3 hours. The reaction mixture was diluted with water (50 mL) and extracted with ether (3×25 mL). The ether extracts were combined, dried over $Na_2SO_4$, filtered and concentrated. The residue was purified by flash chromatography on silica gel eluting with 20% ethyl acetate/hexane to afford 81 mg (62%) of 4-isopropyl-6-methoxy-2-[1-(4-chlorophenyl)-3-cyanopyrazol-5-yl-oxymethyl]-1,2-benzisothiazol-3(2H)-one 1,1-dioxide (Formula I: $R^1$=4-Cl—Ph; $R^2$=CN; $R^3$=H; $R^4$=CH(CH$_3$)$_2$; $R^5$=6-OCH$_3$), m.p. 135° C.

EXAMPLE 47

The cesium salt of 1-phenyl-3-trifluoromethyl-5-hydroxypyrazole [prepared from 1-phenyl-3-trifluoromethyl-5-hydroxypyrazole (0.714 g, 0.312 mmol) and $Cs_2CO_3$ (0.509 g, 0.156 mmol)] was suspended in DMF (20 ml) and treated with 2-chloromethyl-4, 6-diethoxy-1,2-benzisothiazol-3 (2H)-one 1,1-dioxide (0.5 g, 0.156 mmol). The reaction mixture was stirred at room temperature for 24 hours, then was poured onto ice-water and was extracted with ethyl acetate (300 mL). The organic layer was washed with water, then brine and then was dried over $MgSO_4$. The solvent was removed and the residue was purified by flash chromatography on silica gel eluting with $CH_2Cl_2$ to afford 0.57 g (71%) of 4,6-diethoxy-2-[1-phenyl-3-trifluoromethylpyrazol-5-yl-oxymethyl]-1,2-benzisothiazol-3(2H)-one 1,1-dioxide (Formula I: $R^1$=Ph; $R^2$=CF$_3$; $R^3$=H; $R^4$=OEt; $R^5$=6-OEt), m.p. 159°–160° C.

EXAMPLE 48

A mixture of 2-bromomethyl-4-isopropyl-6-methoxy-1,2-benzisothiazol-3(2H)-one 1,1-dioxide (291.4 mg, 0.84 mmol), KF (48.8 mg, 0.84 mmol), DMF (10 mL) and 2,4-dihydro-2-benzyl-5-trifluoromethyl-3H-pyrazol-3-one (Formula III: $R^1$=CH$_2$Ph; $R^2$=CF$_3$; $R^3$=H) (200 mg, 0.84 mmol) was stirred at room temperature for 3 hours. The reaction mixture was diluted with water (50 mL) and extracted with ether (3×50 mL). The ether layers were combined, dried over $Na_2SO_4$, filtered and concentrated. The residue was purified by flash chromatography on silica gel eluting with 10% ethyl acetate/hexane to afford 130 mg of 4-isopropyl-6-methoxy-2-[1-benzyl-3-trifluoromethylpyrazol-5-yl-oxymethyl]-1,2-benzisothiazol-3(2H)-one 1,1-dioxide (Formula I: $R^1$=benzyl; $R^2$=CF$_3$; $R^3$=H; $R^4$=CH(CH$_3$)$_2$; $R^5$=6-OCH$_3$), m.p. 116°–118° C.

EXAMPLE 49

(a)

To a mixture of ethyl trifluoroacetoacetate (5.0 g, 27.2 mmol) in acetic acid (50 mL) was added 2,4-dichlorophenylhydrazine (4.82 g, 27.2 mmol). The reaction mixture was refluxed for 22 hours and then was diluted with water (50 mL), neutralized with 2N NaOH and extracted with EtOAc (3×50 mL). The EtOAc extracts were combined, dried over $Na_2SO_4$, filtered and concentrated to afford 5.51 g (70%) of 2,4-dihydro-2-(2,4-dichlorophenyl)-5-trifluoromethyl-3H-pyrazol-3-one (Formula III: $R^1$=2,4-Cl$_2$—Ph; $R^2$=CF$_3$; $R^3$=H).

(b)

A mixture of 2-bromomethyl-4-isopropyl-6-methoxy-1,2-benzisothiazol-3(2H)-one 1,1-dioxide (280 mg, 0.8 mmol), 2,4-dihydro-2-(2,4-dichlorophenyl)-5-trifluoromethyl-3H-pyrazol-3-one (240 mg, 0.8 mmol), KF (46 mg, 0.8 mmol) and DMF (10 mL) was stirred at room temperature overnight. The reaction mixture was diluted with water (100 mL) and extracted with $Et_2O$ (3×50 mL). The combined ether extracts were dried over $Na_2SO_4$, filtered and concentrated to afford, after recrystallization from $CH_2Cl_2$/hexane, 282 mg of 4-isopropyl-6-methoxy-2-[1-(2,4-dichlorophenyl)-3-trifluoromethylpyrazol-5-yl-oxymethyl]-1,2-benzisothiazol-3(2H)-one 1,1-dioxide (Formula I: $R^1$=2,4-Cl$_2$—Ph; $R^2$=CF$_3$; $R^3$=H; $R^4$=CH(CH$_3$)$_2$; $R^5$=6-OCH$_3$), m.p. 145°–147° C.

EXAMPLE 50

(a)

To a mixture 2,4-dichloroaniline (1.78 g, 15 mmol) in water (10 mL) and HCl (3 mL) at 0° C. was added $NaNO_2$ (1 g, 15 mmol) in water (3 mL). The reaction mixture was stirred for 30 minutes and then was added to diethyl 2-cyanosuccinate (3.1 g) in pyridine (60 mL). The reaction mixture was stirred at room temperature for 1.5 hours and then triethylamine (18.6 mL) and 2% NaOH (32 mL) were added and the mixture was stirred for another 2.5 hours. The reaction mixture was poured onto ice, acidified with HCl and a solid formed which was collected by filtration. The solid was dissolved in 4N NaOH and ether and then the organic layer was separated and the aqueous layer was washed with ether (2×100 mL). The aqueous layer was acidified with HCl and then was extracted with ether (3×100 mL). The ether layers were combined, dried over $Na_2SO_4$, treated with activated carbon, filtered and concentrated to afford 750 mg of 2,4-dihydro-2-(2,4-dichlorophenyl)-5-cyano-3H-pyrazol-3-one (Formula III: $R^1$=2,4-$Cl_2$—Ph; $R^2$=CN; $R^3$=H).

(b)

A mixture of 2-bromomethyl-4-isopropyl-6-methoxy-1,2-benzisothiazol-3(2H)-one 1,1-dioxide (410 mg, 1.18 mmol), 2,4-dihydro-2-(2,4-dichlorophenyl)-5-cyano-3H-pyrazol-3-one (300 mg, 1.18 mmol), KF (68.44 mg, 1.18 mmol) and DMF (20 mL) was stirred at room temperature overnight. The reaction mixture was diluted with water (100 mL) and was extracted with ether (3×50 mL). The ether extracts were combined, dried over $Na_2SO_4$, filtered and concentrated. The residue was purified by flash chromatography on silica gel eluting with 20% ethyl acetate/hexane to afford 310 mg of 4-isopropyl-6-methoxy-2-[1-(2, 4-dichlorophenyl)-3-cyanopyrazol-5-yl-oxymethyl]-1,2-benzisothiazol-3(2H)-one 1,1-dioxide (Formula I: $R^1$=2,4-$Cl_2$—Ph; $R^2$=CN; $R^3$=H; $R^4$=CH$(CH_3)_2$; $R^5$=6-OCH$_3$), m.p. 183°–184° C.

EXAMPLE 51

(a)

A mixture of ethyl trifluoroacetoacetate (5 g, 27.2 mmol), 3-chlorophenylhydrazine hydrochloride (4.86 g, 27.2 mmol) and acetic acid (50 mL) was heated at 100° C. overnight. The reaction mixture was concentrated in vacuo, $CH_2Cl_2$ (80 mL) and hexane (40 mL) were added to the residue and the solid which formed was collected by filtration to afford 3.11 g of 2,4-dihydro-2-(3-chlorophenyl)-5-trifluoromethyl-3H-pyrazol-3-one (Formula III: $R^1$=3-Cl—Ph; $R^2$=CF$_3$; $R^3$=H).

(b)

A mixture of 2-bromomethyl-4-isopropyl-6-methoxy-1,2-benzisothiazol-3(2H)-one 1,1-dioxide (600 mg, 1.72 mmol), 2,4-dihydro-2-(3-chlorophenyl)-5-trifluoromethyl-3H-pyrazol-3-one (473 mg, 1.8 mmol), KF (197 mg, 3.4 mmol) and DMF (7 mL) was stirred at 20° C. for 2 hours. Water was added to the reaction mixture and then the mixture was extracted with ether (3×). The ether extracts were combined and concentrated and then the residue was purified by column chromatography on silica gel eluting with $CH_2Cl_2$/hexane (2/1) to afford, after recrystallization from EtOAc/hexane, 494 mg (54%) of 4-isopropyl-6-methoxy-2-[1-(3-chlorophenyl)-3-trifluoromethylpyrazol-5-yl-oxymethyl]-1,2-benzisothiazol-3(2H)-one 1,1-dioxide (Formula I: $R^1$=3-Cl—Ph; $R^2$=CF$_3$; $R^3$=H; $R^4$=CH$(CH_3)_2$; $R^5$=6-OCH$_3$), m.p. 137°–139° C.

EXAMPLE 52

(a)

A mixture of 2,4-dihydro-2-phenyl-5-hydroxy-3H-pyrazol-3-one (1.58 g, 9 mmol) and POBr3 (2.84 g, 9.9 mmol) was heated at 100° C. in a sealed tube for 3 hours. Ice-water was added to the reaction mixture, followed by NaHCO$_3$ until a pH of 7 was obtained. The mixture was extracted with $CH_2Cl_2$ (4×), dried over $Na_2SO_4$ and concentrated. The residue was purified by column chromatography on silica gel eluting with ethyl acetate/hexane to afford 630 mg of the product which was slurried in $CH_2Cl_2$ and collected by filtration to afford 580 mg of 2,4-dihydro-2-phenyl-5-bromo-3H-pyrazol-3-one (Formula III: $R^1$=Ph; $R^2$=Br; $R^3$=H).

(b)

A mixture 2-bromomethyl-4-isopropyl-6-methoxy-1,2-benzisothiazol-3(2H)-one 1,1-dioxide (696 mg, 2 mmol), KF (232 mg, 4 mmol), DMF (8 mL) and 2,4-dihydro-2-phenyl-5-bromo-3H-pyrazol-3-one (478 mg, 2 mmol) was stirred at 20° C. for 2 hours. Ice-water was added to the reaction mixture and then the mixture was extracted with ether, dried and concentrated. The residue was purified by flash chromatography (3×) on silica gel eluting with ethyl acetate/hexane (1/5) to afford, after recrystallization from ethyl acetate/hexane, 344 mg (34%) of 4-isopropyl-6-methoxy-2-[1-phenyl-3-bromopyrazol-5-yl-oxymethyl]-1,2-benzisothiazol-3(2H)-one 1,1-dioxide (Formula I: $R^1$=Ph; $R^2$=Br; $R^3$=H; $R^4$=CH$(CH_3)_2$; $R^5$=6-OCH$_3$), m.p. 110°–113° C.

EXAMPLE 53

(a)

A mixture of ethyl trifluoroacetoacetate (630.6 mg, 3.43 mmol), cyclohexylhydrazine hydrochloride (516 mg, 3.43 mmol), methanol (10 mL) and concentrated HCl (10 drops) was refluxed overnight. The reaction mixture was cooled to room temperature, diluted with water (150 mL) and extracted with ether (3×50 mL). The ether extracts were combined, dried over $Na_2SO_4$, filtered and concentrated to afford, after recrystallization from hexane, 355 mg (45%) of 2,4-dihydro-2-cyclohexyl-5-trifluoromethyl-3H-pyrazol-3-one (Formula III: $R^1$=cyclohexyl; $R^2$=CF$_3$; $R^3$=H).

(b)

A mixture of 2-bromomethyl-4-isopropyl-6-methoxy-1,2-benzisothiazol-3(2H)-one 1,1-dioxide (416.4 mg, 1.2 mmol), 2,4-dihydro-2-cyclohexyl-5-trifluoromethyl-3H-pyrazol-3-one (0.282 g, 1.2 mmol), KF (69.6 mg, 0.12 mmol) and DMF (15 mL) was stirred at room temperature overnight. The reaction mixture was diluted with water (100 mL), extracted with ether and the ether extracts were dried over $Na_2SO_4$, filtered and concentrated to afford 0.2038 g (34%) of 4-isopropyl-6-methoxy-2-[1-cyclohexyl-3-trifluoromethyl lpyrazol-5-yl-oxymethyl]-1,2-benzisothiazol-3(2H)-one 1,1-dioxide (Formula I: $R^1$=cyclohexyl; $R^2$=CF$_3$; $R^3$=H; $R^4$=CH$(CH_3)_2$; $R^5$=6-OCH).

EXAMPLE 54

2-(1-Phenyl-4-methoxycarbonylimidazol-2-yl-thiomethyl)-1,2-benzisothiazol-3(2H)-one 1,1-dioxide.

Biological Test Results

Representative examples of the compounds of the invention have been found to possess valuable pharmacological properties. In particular, they have been found to inhibit the activity of serine proteases, specifically human leukocyte elastase, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

The pharmacological properties of representative examples of the compounds of the invention were demonstrated by the following conventional in vitro biological test procedure.

The test compound (inhibitor) is dissolved in DMSO in a vial to produce an inhibitor stock solution which has a concentration in the range of 200–1000 μM. The inhibitor stock solution is diluted (1:4, 1:16 and 1:64) into assay vials (vials 1, 2 and 3 respectively) containing 2.4 mL of buffer solution (50 mM N-[2-hydroxyethyl] piperazine-N'-[2-ethanesulfonic acid]/NaOH, 500 mM NaCl, pH 7.8 at 25° C.) and DMSO is added so that the total volume in each vial is 3.2 mL. 70 μL, 50 μL, 35 μL and 25 μL of inhibitor from assay vial 1 is placed into the first four wells of a 96-well microtiter plate and each well is made up to 90 μL total volume with the addition of a 25% DMSO/buffer solution. The inhibitor from assay vials 2 and 3 is processed in a similar manner and placed in wells 5–12 respectively to afford a total of 12 different inhibitor concentrations. Four wells (wells 13–16) containing 90 μL of the 25% DMSO/buffer solution but no inhibitor are also run simultaneously with the inhibited wells as a control. 150 μL of substrate solution (prepared by the addition of 500 μL of the human leukocyte elastase (HLE) substrate MeOSuc-Ala-Ala-Pro-Val-pNA (18.7 mM in DMSO) to 19.5 mL of buffer solution) is then added simultaneously into each of the 16 wells and the solution in each well was thoroughly mixed.

The 96-well microtiter plate is placed into a Microplate Reader #89815A spectrophotometer and 110 μL of the enzyme solution (prepared as follows: a mixture of 20 mL of buffer solution and 20 mg of bovine serum albumen is gently vortexed in a scintillation vial and 5 μL HLE stock solution (1 mg/mL dissolved in deionized water) is added) is added simultaneously to each of the 16 wells. Each of the solutions in the wells is throughly mixed and then the time-dependent absorbance data is collected at an absorbance of 410 nM until the assay is complete. It should be noted that although this assay method can be done manually, it is preferred to perform the assay robotically using a Hewlett Packard MicroAssay System Robot. the absorbance versus time data thus obtained affords curves the final slope of which is equal to the final steady-state velocities ($V_F$). Using the program ENZFITTER (Elsevier software), the progress curves for the four control assays ([I]=0 are fit by linear regression to yield the enzyme reaction velocity values in the absences of inhibitor ($V_o$) which are averaged to produce a single fixed value. The inhibition constant $K_i$(nM) is then obtained from a plot of $$\frac{[I]}{1 - V_F/V_o} \text{ versus } V_o/V_F$$

which affords a linear plot wherein:

$$\text{slope} = K_i \left( 1 + \frac{[S]}{Km} \right)$$

and [S] is the concentration of the substrate and $K_m$ is the Michaelis constant.

Table I summarizes the results obtained from the testing of compounds of the invention for human leukocyte elastase inhibitory activity.

TABLE I

| Example No. | $K_i$ (nM) |
|---|---|
| 1 | 0.730 |
| 2 (b) | 0.470 |
| 3 | 0.068 |
| 4 (b) | 0.440 |
| 5 (b) | 0.920 |
| 6 (c) | 0.145 |
| 7 | 0.076 |
| 8 (b) | 0.110 |
| 9 | 0.780 |
| 10 (b) | 0.024 |
| 11 (c) | 0.089 |
| 12 | 0.077 |
| 13 | 0.120 |
| 14 (c) | 0.190 |
| 15 (b) | 0.130 |
| 16 (b) | 1.60 |
| 17 (b) | 0.036 |
| 18 (b) | 0.220 |
| 19 (c) | 0.820 |
| 20 (c) | 0.037 |
| 21 | 0.310 |
| 22 (b) | 0.180 |
| 23 (b) | 0.065 |
| 24 (c) | 0.026 |
| 25 | 0.100 |
| 27 (b) | 0.150 |
| 28 (c) | 0.089 |
| 29 (b) | 0.082 |
| 30 (b) | 0.070 |
| 31 (b) | 0.143 |
| 32 (c) | 0.055 |
| 33 (b) | 0.100 |
| 34 (b) | 0.027 |
| 35 | 0.014 |
| 36 (b) | 0.029 |
| 37 (f) | 0.081 |
| 38 (d) | 0.180 |
| 39 (a) | 1.90 |
| 39 (c) | 0.074 |
| 42 (b) | 0.081 |
| 45 (b) | 0.061 |
| 46 | 0.190 |
| 47 | 0.500 |
| 48 | 39 |
| 50 (b) | 0.058 |
| 51 (b) | 0.130 |
| 52 (b) | 0.066 |
| 54 | 153 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

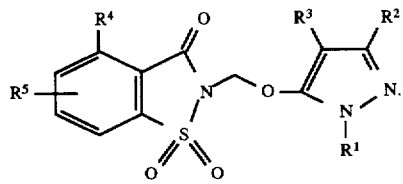

wherein:

$R^1$ is lower-alkyl, phenyl or phenyl substituted by from one to three, the same or different, substituents selected from the group consisting of nitro, halogen, lower-alkoxy, hydroxy, trifluoromethyl and lower-alkyl; a 5- or 6-membered monocyclic aromatic heterocycle which contains from one to two nitrogen atoms or said 5- or 6-membered monocyclic aromatic heterocycle substituted on any available carbon atom thereof by nitro, halogen, lower-alkoxy, trifluoromethyl, hydroxy or lower-alkyl; a 9- or 10-membered bicyclic aromatic heterocycle which contains from one to two nitrogen atoms or said 9- or 10-membered bicyclic aromatic heterocycle substituted on any available carbon atom thereof by nitro, halogen, lower-alkoxy, trifluoromethyl, hydroxy or lower-alkyl; phenyl-lower-alkyl, or cycloalkyl;

$R^2$ is hydrogen, lower-alkyl, lower-alkoxy, phenyl or phenyl substituted by from one to five, the same or different, substituents selected from the group consisting of halogen, lower-alkyl, lower-alkoxy, nitro, hydroxy and trifluoromethyl; trihalomethyl, lower-alkoxycarbonyl, pyridyl, carboxy, —C(O)N(R) (alkylene)—NB wherein R is hydrogen or lower-alkyl and NB is 1-pyrrolidinyl or dilower-alkylamino; halogen, or cyano;

$R^3$ is hydrogen, halogen, or lower-alkyl;

$R^4$ is lower-alkyl, lower-alkoxy, or cycloalkyl; and $R^5$ is hydrogen, or from one to two substituents in any of the 5-, 6-, or 7-positions selected from the group consisting of lower-alkoxy, —O—$(CH_2)_n$-[5-(($CH_2)_n$—N(lower-alkyl)$_2$)-2-furanyl], benzyloxycarbonyl-lower-alkoxy, lower-alkoxycarbonyl-lower-alkoxy, carboxylower-alkoxy, hydroxy, —O—(lower-alkyl)—C(O)N(R') (alkylene)N(lower-alkyl)$_2$, —O—$(CH_2)_n$-[5-(C(O)OCH$_2$-phenyl-R")-2-furanyl], —O—$(CH_2)_n$-(5-carboxy-2-furanyl), and —O—$(CH_2)_n$-[5-(C(O)N(R''')(alkylene)-N(lower-alkyl)$_2$)-2-furanyl]; wherein n is an integer from one to four; R' is hydrogen or lower-alkyl; R" is hydrogen, lower-alkyl, or lower-alkoxy; and R''' is hydrogen or lower-alkyl; or a pharmaceutically acceptable acid-addition salt of basic members thereof, or a pharmaceutically acceptable base-addition salt of acidic members thereof.

2. A compound according to claim 1 wherein:

$R^1$ is lower-alkyl, phenyl or phenyl substituted by from one to two, the same or different, substituents selected from the group consisting of nitro, halogen, and lower-alkoxy; a 5- or 6-membered monocyclic aromatic heterocycle selected from the group consisting of pyridyl, pyridazinyl, pyrazinyl, pyrimidinyl, pyrrolyl, pyrazolyl, and imidazolyl or said 5- or 6-membered monocyclic aromatic heterocycle substituted on any available carbon atom thereof by halogen, trifluoromethyl, or lower-alkyl; a 9- or 10-membered bicyclic aromatic heterocycle selected from the group consisting of quinolinyl, isoquinolinyl, benzimidazolyl, quinoxalinyl, quinazolinyl, indolyl, and indazolyl or said 9- or 10-membered bicyclic aromatic heterocycle substituted on any available carbon atom thereof by halogen, trifluoromethyl, or lower-alkyl; phenyl-lower-alkyl, or cycloalkyl; and $R^2$ is hydrogen, lower-alkyl, phenyl (or phenyl substituted by from one to five, the same or different, substituents selected from the group consisting of halogen, lower-alkyl, lower-alkoxy, and hydroxy; trihalomethyl, lower-alkoxycarbonyl, pyridyl, carboxy, —C(O)N(R) (alkylene)—NB wherein R is hydrogen or lower-alkyl and NB is 1-pyrrolidinyl or dilower-alkylamino; halogen, or cyano.

3. A compound according to claim 2 wherein:

$R^2$ is hydrogen, lower-alkyl, phenyl or phenyl substituted by from one to five, the same or different, halogen substituents; trihalomethyl, lower-alkoxycarbonyl, pyridyl, carboxy, —C(O)N(R)(alkylene)—NB wherein R is hydrogen or lower-alkyl and NB is 1-pyrrolidinyl or dilower-alkylamino; halogen, or cyano;

$R^3$ is hydrogen or halogen;

$R^4$ is lower-alkyl or lower-alkoxy; and $R^5$ is from one to two substituents in any of the 5-, 6- or 7- positions selected from the group consisting of lower-alkoxy, —O—$(CH_2)_n$-[5-(($CH_2)_n$—N(lower-alkyl)$_2$)-2-furanyl] benzyl oxycarbonyl-lower-alkoxy, carboxylower-alkoxy, hydroxy, —O—(lower-alkyl)—C(O)N(R')(alkylene)N(lower-alkyl)$_2$, —O—$(CH_2)_n$-[5-(C(O)OCH$_2$-phenyl-R")-2-furanyl], —O—$(CH_2)_n$-

(5-carboxy-2-furanyl), and —O—(CH$_2$)$_n$-[5-(C(O)N(R''')(alkylene)-N-(lower-alkyl)$_2$)-2-furanyl]; wherein n is one; R' is lower-alkyl; R" is lower-alkoxy; and R''' is lower-alkyl.

4. A compound according to claim 3 wherein:

R$^1$ is lower-alkyl, phenyl or phenyl substituted by from one to two, the same or different, substituents selected from the group consisting of nitro, halogen, and lower-alkoxy; a 5- or 6-membered monocyclic aromatic heterocycle selected from the group consisting of pyridyl, pyridazinyl, and pyrimidinyl or said 5- or 6-membered monocyclic aromatic heterocycle substituted on any available carbon atom thereof by halogen, trifluoromethyl, or lower-alkyl; quinolinyl, isoquinolinyl, phenyl-lower-alkyl, or cycloalkyl; and R$^5$ is one substituent in the 6-position selected from the group consisting of lower-alkoxy, —O—(CH$_2$)$_n$-[5-((CH$_2$)$_n$—N(lower-alkyl)$_2$)-2-furanyl], benzyloxycarbonyl-lower-alkoxy, carboxylower-alkoxy, hydroxy, —O—(lower-alkyl)—C(O)N(R')-(alkylene)N(lower-alkyl)$_2$, —O—(CH$_2$)$_n$-[5-(C(O)OCH$_2$-phenyl-R")-2-furanyl], —O—(CH$_2$)$_n$-(5-carboxy-2-furanyl), and —O—(CH$_2$)$_n$-[5-(C(O)N(R''')(alkylene)-N-(lower-alkyl)$_2$)-2-furanyl]; wherein n is one; R' is lower-alkyl; R" is lower-alkoxy; and R''' is lower-alkyl.

5. A compound according to claim 4 wherein R$^3$ is hydrogen or chloro; and R$^4$ is isopropyl or ethoxy.

6. A compound according to claim 5 wherein R$^2$ is hydrogen, methyl, phenyl, pentafluorophenyl, trifluoromethyl, ethoxycarbonyl, 4-pyridyl, carboxy, —C(O)N(R)(CH$_2$)$_2$—NB wherein R is hydrogen or methyl and NB is 1-pyrrolidinyl or diethylamino; chloro, tertbutoxycarbonyl, or cyano.

7. A compound according to claim 6 wherein R$^1$ is methyl, phenyl or phenyl substituted by from one to two, the same or different, substituents selected from the group consisting of nitro, chloro, and methoxy; a 5- or 6-membered monocyclic aromatic heterocycle selected from the group consisting of 2-pyridyl, 3-pyridyl, 4-pyridyl, pyridazinyl, and pyrimidinyl or said 5- or 6-membered monocyclic aromatic heterocycle substituted on any available carbon atom thereof by chloro, trifluoromethyl, or methyl; quinolinyl, benzyl, or cyclohexyl.

8. A compound according to claim 7 wherein R$^5$ is one substituent in the 6-position selected from the group consisting of methoxy, ethoxy, —O—(CH$_2$)-[5-((CH$_2$)—N(CH$_3$)$_2$)-2-furanyl], 3-(benzyloxycarbonyl)propoxy, 3-(carboxy)propoxy, —O—CH$_2$C(CH$_3$)$_2$ CO$_2$CH$_2$Ph, —O—CH$_2$C(CH$_3$)$_2$CO$_2$H, hydroxy, 5-(benzyloxycarbonyl)pentyloxy, 5-(carboxy)pentyloxy, —O—(CH$_2$)$_2$C(CH$_3$)$_2$CO$_2$CH$_2$Ph, —O—(CH$_2$)$_2$C(CH$_3$)$_2$CO$_2$H, —O—(CH$_2$)$_3$—C(O)N(CH$_3$)(CH$_2$)$_2$N(Et)$_2$, —O—(CH$_2$)$_5$-C(O)Et)(CH$_2$)$_2$N(Et)$_2$, —O—(CH$_2$)-[5-(C(O)OCH$_2$-phenyl-4-OCH$_3$)-2-furanyl], —O—(CH$_2$)-(5-carboxy-2-furanyl), and —O—(CH$_2$)-[5-(C(O)N(Et)(CH$_2$)$_2$-N-(Et)$_2$)-2-furanyl].

9. A compound according to claim 8 selected from the group consisting of:

4-isopropyl-6-[3-carboxy)propoxy]-2-(1-phenyl-3-trifluoromethylpyrazol-5-yl-oxymethyl)-1,2-benzisothiazol-3(2H)-one 1,1-dioxide;

4-isopropyl-6-[(2-carboxy-2-methyl)propoxy]-2-(1-phenyl-3-trifluoromethylpyrazol-5-yl-oxymethyl)-1,2-benzisothiazol-3(2H)-one 1,1-dioxide;

4-isopropyl-6-[3-(carboxy)propoxy]-2-[1-(4-chlorophenyl)-3-trifluoromethylpyrazol-5-yl-oxymethyl)-1,2-benzisothiazol-3(2H)-one 1,1-dioxide; and 4-isopropyl-6-[5-[Et$_2$N(CH$_2$)$_2$N(Et)C(O)]pentyloxy]-2-(1-phenyl -3-trifluoromethylpyrazol-5-yl-oxymethyl)-1,2-benzisothiazol-3(2H)-one 1,1-dioxide.

10. A pharmaceutical composition for the treatment of degenerative diseases which comprises an effective proteolytic enzyme inhibiting amount of a compound according to claim 1 together with a pharmaceutically acceptable carrier, adjuvant, diluent or vehicle.

11. A pharmaceutical composition for the treatment of degenerative diseases which comprises an effective proteolytic enzyme inhibiting amount of a compound according to claim 2 together with a pharmaceutically acceptable carrier, adjuvant, diluent or vehicle.

12. A pharmaceutical composition for the treatment of degenerative diseases which comprises an effective proteolytic enzyme inhibiting amount of a compound according to claim 3 together with a pharmaceutically acceptable carrier, adjuvant, diluent or vehicle.

13. A pharmaceutical composition for the treatment of degenerative diseases which comprises an effective proteolytic enzyme inhibiting amount of a compound according to claim 4 together with a pharmaceutically acceptable carrier, adjuvant, diluent or vehicle.

14. A pharmaceutical composition for the treatment of degenerative diseases which comprises an effective proteolytic enzyme inhibiting amount of a compound according to claim 5 together with a pharmaceutically acceptable carrier, adjuvant, diluent or vehicle.

15. A pharmaceutical composition for the treatment of degenerative diseases which comprises an effective proteolytic enzyme inhibiting amount of a compound according to claim 6 together with a pharmaceutically acceptable carrier, adjuvant, diluent or vehicle.

16. A pharmaceutical composition for the treatment of degenerative diseases which comprises an effective proteolytic enzyme inhibiting amount of a compound according to claim 7 together with a pharmaceutically acceptable carrier, adjuvant, diluent or vehicle.

17. A pharmaceutical composition for the treatment of degenerative diseases which comprises an effective proteolytic enzyme inhibiting amount of a compound according to claim 8 together with a pharmaceutically acceptable carrier, adjuvant, diluent or vehicle.

18. A pharmaceutical composition for the treatment of degenerative diseases which comprises an effective proteolytic enzyme inhibiting amount of a compound according to claim 9 together with a pharmaceutically acceptable carrier, adjuvant, diluent or vehicle.

19. A method for the treatment of degenerative diseases which comprises administering to a patient in need of such treatment an effective proteolytic enzyme inhibiting amount of a compound according to claim 1.

20. A method for the treatment of degenerative diseases which comprises administering to a patient in need of such treatment an effective proteolytic enzyme inhibiting amount of a compound according to claim 2.

21. A method for the treatment of degenerative diseases which comprises administering to a patient in need of such treatment an effective proteolytic enzyme inhibiting amount of a compound according to claim 3.

22. A method for the treatment of degenerative diseases which comprises administering to a patient in need of such treatment an effective proteolytic enzyme inhibiting amount of a compound according to claim 4.

23. A method for the treatment of degenerative diseases which comprises administering to a patient in need of such treatment an effective proteolytic enzyme inhibiting amount of a compound according to claim 5.

24. A method for the treatment of degenerative diseases which comprises administering to a patient in need of such treatment an effective proteolytic enzyme inhibiting amount of a compound according to claim 6.

25. A method for the treatment of degenerative diseases which comprises administering to a patient in need of such treatment an effective proteolytic enzyme inhibiting amount of a compound according to claim 7.

26. A method for the treatment of degenerative diseases which comprises administering to a patient in need of such treatment an effective proteolytic enzyme inhibiting amount of a compound according to claim 8.

27. A method for the treatment of degenerative diseases which comprises administering to a patient in need of such treatment an effective proteolytic enzyme inhibiting amount of a compound according to claim 9.

28. A method according to claim 19 wherein said degenerative diseases are selected from emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

29. A method according to claim 28 wherein said degenerative diseases are selected from emphysema, cystic fibrosis, chronic bronchitis, and adult respiratory distress syndrome.

* * * * *